United States Patent
Pan et al.

(10) Patent No.: US 9,682,062 B2
(45) Date of Patent: Jun. 20, 2017

(54) PHARMACEUTICAL COMPOSITIONS AND METHOD FOR INHIBITING ANGIOGENESIS

(71) Applicant: Industrial Technology Research Institute, Hsinchu (TW)

(72) Inventors: I-Horng Pan, Hsinchu (TW); Hsin-Jan Yao, Yunlin County (TW); Mei-Wei Lin, Zhubei (TW); I-Huang Lu, Zhudong Township (TW); Hsin-Chieh Wu, Hsinchu (TW); Hsiang-Wen Tseng, New Taipei (TW); Ching-Huai Ko, Changhua (TW); Chun-Chung Wang, Kaohsiung (TW); Zong-Keng Kuo, New Taipei (TW); Shyh-Horng Lin, Kaohsiung (TW); Yi-Cheng Cheng, Hsinchu (TW); Tien-Soung Tong, Taichung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 147 days.

(21) Appl. No.: 14/133,213

(22) Filed: Dec. 18, 2013

(65) Prior Publication Data
US 2014/0170250 A1 Jun. 19, 2014

(30) Foreign Application Priority Data

Dec. 19, 2012 (TW) .............................. 101148230 A

(51) Int. Cl.
| | | |
|---|---|---|
| A61K 36/15 | (2006.01) |
| A61K 36/185 | (2006.01) |
| A61K 31/365 | (2006.01) |
| A61K 36/14 | (2006.01) |
| A61K 31/7048 | (2006.01) |

(52) U.S. Cl.
CPC ........ *A61K 31/365* (2013.01); *A61K 31/7048* (2013.01); *A61K 36/14* (2013.01)

(58) Field of Classification Search
None
See application file for complete search history.

(56) References Cited

U.S. PATENT DOCUMENTS

| 7,807,803 | B2 | 10/2010 | Krieg |
| 8,158,592 | B2 | 4/2012 | Krieg et al. |
| 8,980,261 | B2* | 3/2015 | Tavazoie ............... 424/130.1 |
| 2006/0079575 | A1* | 4/2006 | Lin ................. A61K 36/23 514/464 |
| 2006/0228426 | A1 | 10/2006 | Cyr |
| 2010/0323041 | A1 | 12/2010 | Cyr |

FOREIGN PATENT DOCUMENTS

| JP | 2014-122216 A | 7/2014 |
| KR | 10-2007-0008230 A | 1/2007 |
| KR | 10-0673574 B1 | 1/2007 |
| KR | 10-0799266 B1 | 1/2008 |
| KR | 10-0911623 B1 | 8/2009 |
| KR | 10-2009-0106274 A | 10/2009 |
| WO | WO2014086379 A1 * | 6/2014 |

OTHER PUBLICATIONS

Japanese Office Action for corresponding application No. 2013-257009, dated Dec. 16, 2014.
M. Novelo et al., "Cytotoxic Constitutents From Hyptis Verticillata", Journal of Natural Products, Oct. 1993, vol. 56, No. 10, pp. 1728-1736.
Kuo et al., "Yatein from Chamaecyparis obtusa suppresses herpes simplex virus type 1 replication in HeLa cells by interruption the immediate-early gene expression", Antiviral Research, vol. 70, 2006, pp. 112-120.
Miyata et al., "Extractives of *Juniperus chinensis* L. I: Isolation of podophyllotoxin and yatein from the leaves of *J. chinensis*", J. Wood Sci., May 6, 1998, vol. 44, pp. 397-400.
Taiwanese Office Action, dated Apr. 25, 2014, for Taiwanese Application No. 101148230.
Ali et al., "Antitumour-promoting and antitumour activities of the crude extract from the leaves of Juniperus chinensis," Journal of Ethnopharmacology, 1996, vol. 53, pp. 165-169.
Huang et al., "A natural compound(ginsenoside Re) isolated from Panax ginseng as a novel angiogenic agent for tissue regeneration," Pharmaceutical Research, Apr. 2005, vol. 22, No. 4, pp. 636-646.
Ju et al., "Comparision between ethanolic and aqueous extracts from Chinese juniper berries for hypoglycaemic and hypolipidemic effects in alloxan-induced diabetic rats," Journal of Ethnopharmacology, 2008, vol. 115, pp. 110-115.
Kim et al., "Anti-obesity Effects of Juniperus chinensis Extract Are Associated with Increased AMP-Activated Protein Kinase Expression and Phosphorylation in the Visceral Adipose Tissue of Rats," Biol. Pharm. Bull, Jul. 2008, vol. 31, No. 7, pp. 1415-1421.
Kimura et al., "Effects of ginseng saponins isolated from Red Ginseng roots on burn wound healing in mice," British Journal of Pharmacology, 2006, vol. 148, pp. 860-870.
Kwon et al., "Widdrol induces cell cycle arrest, associated with MCM down-regulation, in human colon adenocarcinoma cells," Cancer Letters, 2010, vol. 290, pp. 96-103.

(Continued)

*Primary Examiner* — Chris R Tate
*Assistant Examiner* — Randall Winston
(74) *Attorney, Agent, or Firm* — Birch, Stewart, Kolasch & Birch, LLP

(57) ABSTRACT

The disclosure provides a pharmaceutical composition for inhibiting angiogenesis, including an effective amount of an extract of *Juniperus chinensis* or an effective amount of a lignan as an effective ingredient. The pharmaceutical composition may further include a pharmaceutically acceptable carrier or salt. The disclosure also provides a method for inhibiting angiogenesis, including administering an effective amount of an extract of *Juniperus chinensis* or an effective amount of a lignan as an effective ingredient for inhibiting angiogenesis to a subject in need thereof.

2 Claims, 23 Drawing Sheets

(56) References Cited

OTHER PUBLICATIONS

Sengupta et al., "Modulating angiogenesis: the yin and the yang in ginseng," Circulation, Journal of the American Heart Association, Aug. 30, 2004, vol. 110, 10 pages.

Yu et al., "Stability of angiogenic agents, ginsenoside Rgl and Re, isolated from Panax ginseng: in vitro and invivo studies," Journal of Pharmaceutics, 2007, vol. 328, pp. 168-176.

Japanese Office Action, dated Feb. 7, 2017, for Japanese Application No. 2016-020388.

* cited by examiner

US 9,682,062 B2

PHARMACEUTICAL COMPOSITIONS AND METHOD FOR INHIBITING ANGIOGENESIS

CROSS REFERENCE TO RELATED APPLICATION

The present application is based on, and claims priority from, Taiwan Application Serial Number 101148230, filed on Dec. 19, 2012, the disclosure of which is hereby incorporated by reference herein in its entirety.

TECHNICAL FIELD

The technical field relates to pharmaceutical compositions and method for inhibiting angiogenesis.

BACKGROUND

Angiogenesis means a process for forming a new blood vessel near a pre-existing blood vessel. Under a normal physiological mechanism, during the process of a response which can result from a stimulation of signal transduction for angiogenesis, such as wound healing or the menstrual cycle of women, a controlled angiogenesis will occur and be maintained for about 1-2 weeks. However, pathological angiogenesis is not controlled by a normal physiological mechanism. Regulation of angiogenesis plays a very important balancing role in the human body. Under a strong angiogenesis effect, it may result in diabetic retinopathy, rheumatoid arthritis, or may accelerate aggravation or metastasis of a tumor. In addition, when angiogenesis is over-suppressed, it may result in occurrence of diseases related to hemorrhage, apoplexy, cardiovascular diseases, etc. and even affect wound healing of a patient due to a defective coagulation function.

At present, about 19 kinds of angiogenesis inhibitors are used clinically, and indications for these drugs comprise various solid tumors, age-related macular degeneration, choroidal neovascularization, diabetic macular edema, diabetic retinopathy, ocular neoplasm, retinal venous occlusion, telangiectasis, etc. Since angiogenesis is related to various diseases, development of a new angiogenesis inhibitor is a very important research direction and development field at present and in the future.

SUMMARY

The disclosure provides a pharmaceutical composition for inhibiting angiogenesis, comprising: an effective amount of an extract of *Juniperus chinensis* as an effective ingredient.

The disclosure also provides a method for inhibiting angiogenesis, comprising: administering an effective amount of an extract of *Juniperus chinensis* as an effective ingredient for inhibiting angiogenesis to a subject in need thereof.

Furthermore, the disclosure provides a pharmaceutical composition for inhibiting angiogenesis, comprising: an effective amount of a lignan as an effective ingredient, wherein a formula of the lignan is shown as Formula (I):

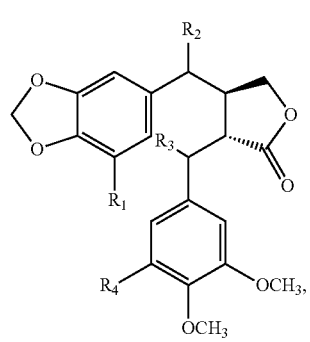

Formula (I)

wherein $R_1$ is —H or —$OCH_3$, $R_2$ is —H or —OH, $R_3$ is —H, —OH or β-O-glucoside, and $R_4$ is —H or —$OCH_3$.

The disclosure also provides a method for inhibiting angiogenesis, comprising: administering an effective amount of a lignan as an effective ingredient for inhibiting angiogenesis to a subject in need thereof, wherein a formula of the lignan is shown as Formula (I):

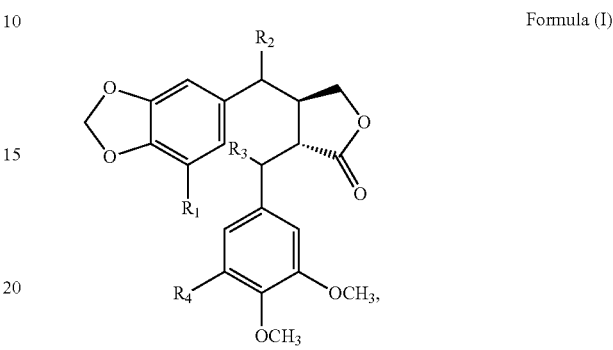

Formula (I)

wherein $R_1$ is —H or —$OCH_3$, $R_2$ is —H or —OH, $R_3$ is —H, —OH or β-O-glucoside, and $R_4$ is —H or —$OCH_3$.

A detailed description is given in the following embodiments with reference to the accompanying drawings.

BRIEF DESCRIPTION OF DRAWINGS

The present disclosure can be more fully understood by reading the subsequent detailed description and examples with references made to the accompanying drawings, wherein.

DETAILED DESCRIPTION

Figure 1:
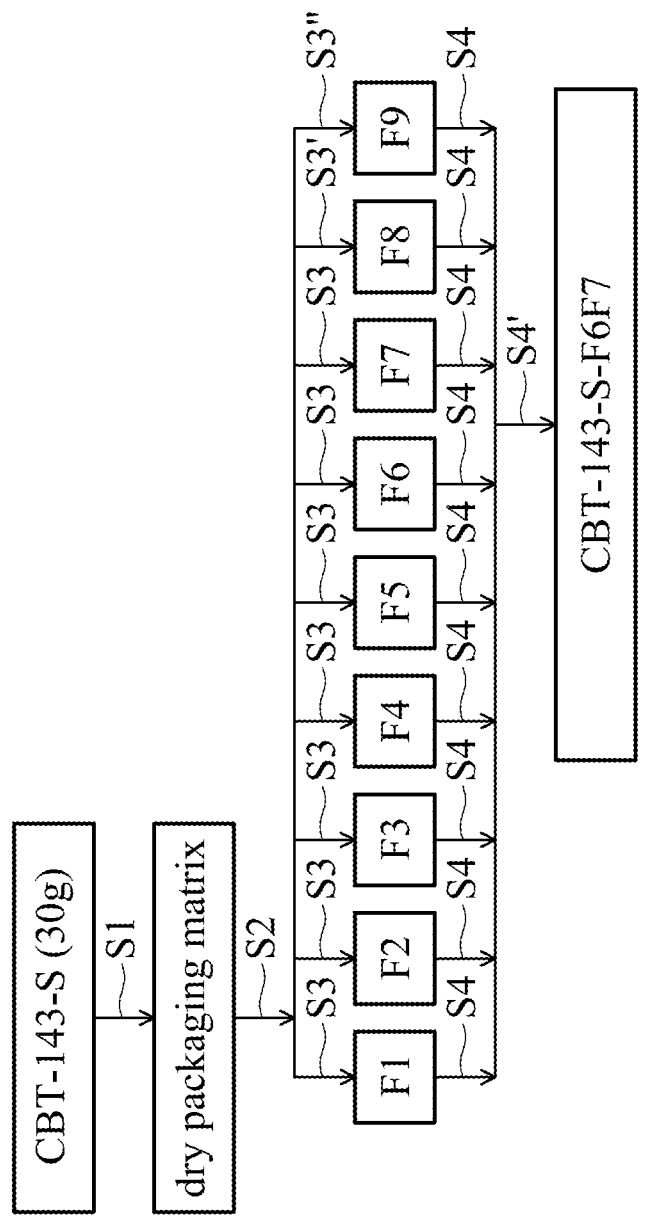
FIG. 1 shows a preparation process for the fractional extract, CBT-143-S-F6F7 according to one embodiment of the disclosure

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The disclosure provides a pharmaceutical composition for inhibiting angiogenesis, which uses an extract of *Juniperus chinensis* as a main effective ingredient, and which has an effect of inhibiting angiogenesis.

The pharmaceutical composition for inhibiting angiogenesis mentioned above may comprise, but is not limited to, an extract of *Juniperus chinensis*, wherein the extract of *Juniperus chinensis* is an active ingredient for inhibiting angiogenesis. In one embodiment, pharmaceutical composition for inhibiting angiogenesis of the present disclosure may further comprise a pharmaceutically acceptable carrier or salt.

In the present disclosure, an example of *Juniperus chinensis* which is used to provide the extract of *Juniperus chinensis* may comprise *Juniperus chinensis* var. Shimpaku, *Juniperus chinensis* L. var. *sargentii* Henry, *Juniperus chinensis* L. var. *chinensis* (proto-variety), *Juniperus chinensis* L. var. *taiwanensis* R. P. Adams & C. F. Hsieh, *Juniperus chinensis* L. var. *kaizuka* Hort. ex Endl., *Juniperus chinensis* L. var. *pyramidalis* (Carr.) Hort. ex Rehd. and/or *Juniperus chinensis* cv. Pfitzeriana Glauca. In one embodiment, the *Juniperus chinensis* which is used to provide the extract of *Juniperus chinensis* is *Juniperus chinensis* L. var. *sargentii* Henry.

The extract of *Juniperus chinensis* may be extracted from a root, a stem/trunk, a branch, a leaf, and/or a combination thereof, but it is not limited thereto. In one embodiment, the extract of *Juniperus chinensis* may be extracted from thin branches and leaves of the *Juniperus chinensis*.

In the present disclosure, a solvent which is used to extract the extract of *Juniperus chinensis* may comprise alcohol (such as methanol, ethanol or propanol), ester (such as ethyl acetate), alkane (such as hexane) or haloalkane (such as chloromethane, chloroethane), but it is not limited thereto. In one embodiment, the extract solvent is ethanol.

In one embodiment, ingredients of the extract of *Juniperus chinensis* of the present disclosure may comprise at least one indicator ingredient, yatein, which has an effect of inhibiting angiogenesis. In another embodiment, ingredients of the extract of *Juniperus chinensis* of the present disclosure may at least comprise yatein which has an effect of inhibiting angiogenesis.

In one embodiment, the extract of *Juniperus chinensis* may be extracted from *Juniperus chinensis* L. var. *sargentii* Henry, and the extract of *Juniperus chinensis* is obtained from using ethanol to extract. In this embodiment, the ingredients of the extract of *Juniperus chinensis* mentioned above may at least comprise yatein. In another embodiment, the extract of *Juniperus chinensis* is obtained from extracting thin branches and leaves of *Juniperus chinensis* L. var. *sargentii* Henry with ethanol. In this embodiment, the ingredients of the extract of *Juniperus chinensis* mentioned above may at least comprise yatein.

The pharmaceutical composition for inhibiting angiogenesis of the present disclosure is used for treating a disease related to angiogenesis. Examples of the disease related to angiogenesis may comprise solid tumors, age related macular degeneration, choroidal neovascularization, diabetic macular edema, diabetic retinopathy, ocular neoplasm, retinal venous occlusion, telangiectasis, etc., but they are not limited thereto.

The disclosure also provides a pharmaceutical composition for inhibiting angiogenesis, which uses a lignan as a main effective ingredient. The pharmaceutical composition for inhibiting angiogenesis mentioned above may comprise, but is not limited to an effective amount of a lignan, wherein a formula of the lignan is shown as Formula (I):

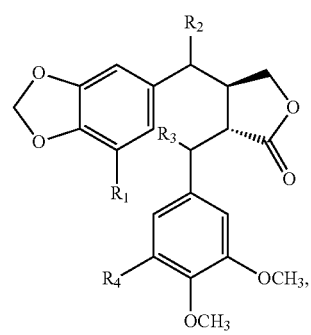

Formula (I)

wherein $R_1$ is —H or —OCH$_3$, $R_2$ is —H or —OH, $R_3$ is —H, —OH or β-O-glucoside, and $R_4$ is —H or —OCH$_3$.

In one embodiment, the foregoing pharmaceutical composition for inhibiting angiogenesis may further comprise a pharmaceutically acceptable carrier or salt.

In one embodiment, the lignan mentioned above may comprise, but is not limited to, yatein, 5'-desmethoxyyatein (bursehernin), 7',7'-dihydroxy bursehernin, 5'-methoxyyatein, podorhizol or podorhizol 4'-o-β-D-glucopyranoside. In one exemplary embodiment, the lignan mentioned above is yatein.

In the preceding pharmaceutical composition for inhibiting angiogenesis of the present disclosure, the pharmaceutically acceptable carrier mentioned above may comprise, but is not limited to, a solvent, a dispersion medium, a coating, an antibacterial and antifungal agent, or an isotonic and absorption delaying agent, etc. which is compatible to pharmaceutical administration. The pharmaceutical composition can be formulated into dosage forms for different administration routes utilizing conventional methods.

Moreover, the pharmaceutically acceptable salt mentioned above may comprise, but is not limited to, inorganic cation salt, such as alkali metal salts such as sodium salt, potassium salt or amine salt, such as alkaline-earth metal salt such as magnesium salt or calcium salt, such as the salt containing bivalent or quadrivalent cation such as zinc salt, aluminum salt or zirconium salt. In addition, the pharmaceutically acceptable salt may also comprise organic salt, such as dicyclohexylamine salt, methyl-D-glucamine, and amino acid salt such as arginine, lysine, histidine, or glutamine.

The pharmaceutical composition of the present disclosure may be administered orally, parenterally by an inhalation spray, or via an implanted reservoir. The parenteral method may comprise subcutaneous, intracutaneous, intravenous, intramuscular, intra-articular, intra-arterial, intrasynovial, intrasternal, intrathecal, and intraleaional, as well as infusion techniques.

An oral composition can comprise, but is not limited to, tablets, capsules, emulsions, and aqueous suspensions, dispersions and solutions.

In addition, the present disclosure also provides a method for inhibiting angiogenesis. The method for inhibiting angiogenesis mentioned above may comprise, but is not limited to, administering an effective amount of an extract of *Juniperus chinensis* as an effective ingredient for inhibiting angiogenesis to a subject in need thereof.

The extract of *Juniperus chinensis* is extracted from *Juniperus chinensis*, and the *Juniperus chinensis* may comprise *Juniperus chinensis* var. Shimpaku, *Juniperus chinensis* L. var. *sargentii* Henry, *Juniperus chinensis* L. var. *chinensis* (proto-variety), *Juniperus chinensis* L. var. *taiwanensis* R. P. Adams & C. F. Hsieh, *Juniperus chinensis* L. var. *kaizuka* Hort. ex Endl., *Juniperus chinensis* L. var. *pyramidalis* (Carr.) Hort. ex Rehd. and/or *Juniperus chinensis* cv. Pfitzeriana Glauca, but it is not limited thereto. In one embodiment, the *Juniperus chinensis* mentioned above is *Juniperus chinensis* L. var. *sargentii* Henry.

In the present disclosure, an extracting part for the *Juniperus chinensis* may comprise a root, a stem/trunk, a branch, a leaf, and/or a combination thereof, but it is not limited thereto. In one embodiment, the foregoing extract of *Juniperus chinensis* is extracted from thin branches and leaves of *Juniperus chinensis*.

In addition, examples of a solvent which is suitable for extracting the extract of *Juniperus chinensis* mentioned above may comprise alcohol (such as methanol, ethanol or propanol), ester (such as ethyl acetate), alkane (such as hexane) or haloalkane (such as dichloromethane, dichloroethane), but it is not limited thereto. In one embodiment, the extract solvent is ethanol.

In one embodiment, ingredients of the foregoing extract of *Juniperus chinensis* may comprise yatein, which has an effect of inhibiting angiogenesis.

In one embodiment, the extract of *Juniperus chinensis* may be extracted from *Juniperus chinensis* L. var. *sargentii* Henry, and the extract of *Juniperus chinensis* is obtained from using ethanol to extract. In this embodiment, ingredients of the extract of *Juniperus chinensis* mentioned above may at least comprise yatein. In another embodiment, the extract of *Juniperus chinensis* is obtained from extracting thin branches and leaves of *Juniperus chinensis* L. var. *sargentii* Henry with ethanol. In this embodiment, ingredients of the extract of *Juniperus chinensis* mentioned above may at least comprise yatein.

Furthermore, the present disclosure provides another method for inhibiting angiogenesis. The method for inhibiting angiogenesis mentioned above may comprise, but is not limited to, administering an effective amount of a lignan as an effective ingredient for inhibiting angiogenesis to a subject in need thereof, wherein a formula of the lignan is shown as Formula (I):

Formula (I)

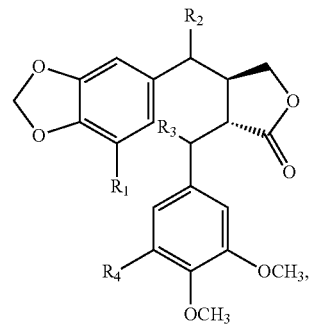

wherein $R_1$ is —H or —OCH$_3$, $R_2$ is —H or —OH, $R_3$ is —H, —OH or β-O-glucoside, and $R_4$ is —H or —OCH$_3$.

In one embodiment, the lignan mentioned above may comprise, but is not limited to, yatein, 5'-desmethoxyyatein (bursehernin), 7',7'-dihydroxy bursehernin, 5'-methoxyyatein, podorhizol or podorhizol 4'-o-β-D-glucopyranoside. In one exemplary embodiment, the lignan mentioned above is yatein.

EXAMPLES

A. Investigation and Determination for an Active Part of *Juniperus chinensis* L. var. *sargentii* Henry About 10 g of dry thin branches and leaves of *Juniperus chinensis* L. var. *sargentii* Henry was immersed in 8- to 10-fold weight of solvent (such as water, ethanol, propanol, ethyl acetate or hexane), and the immersed plant material was extracted at the boiling point of the solvent for 1 hour to obtain an extract solution. After that, the extract solution was filtered with filter paper, concentrated to dry, mixed with pure water and then sonicated to form a suspension. Then, the suspension was lyophilized.

The lyophilized powder was dissolved in an appropriate solvent and an in vitro anti-angiogenesis was performed thereto. The ability of the extract for inhibiting net structure formation of human umbilical vein endothelial cells (HUVEC) in extracellular matrix (ECM) or growth factor reduced Matrigel was analyzed, and the forming level of the tube structure thereof was integrated to be used as an indicator for quantification. The results are shown in Table 1.

TABLE 1

Content of indicator ingredients and activities for inhibiting net structure formation of human umbilical vein endothelial cells of the extracts of thin branches and leaves Juniperus chinensis L. var. sargentii Henry extracted with different solvents.
Plant part: Thin branches and leaves

| Sample name | Yatein (mg/g) | Net structure formation (%) | Note |
|---|---|---|---|
| CBT143-LWH | N.D | 101.1 | Water extract |
| CBT143-LEH | 2.02 | 0.3 | Ethanol extract |
| CBT143-LAH | 2.42 | 0 | Propanol extract |
| CBT143-LTH | 2.63 | 0.2 | Ethyl acetate extract |
| CBT143-LHH | 2.73 | 0.2 | n-Hexane extract |

N.D: Lower than detection limitation

The results showed that water extract is not capable of inhibiting formation of net structure (tube formation), whereas the other solvent extracts are all capable of inhibiting tube formation of endothelial cells.

B. Preparation of Ethanol Extract of *Juniperus chinensis* L. var. *sargentii* Henry 1. Extraction Process for Crude Extract (CBT-143-S)

According to the results shown above, thin branches and leaves of *Juniperus chinensis* L. var. *sargentii* Henry were selected as a target for extraction, and ethanol was selected as the extract solvent. The obtained crude extract was named CBT-143-S, and the preparation process thereof is shown in the following:

(1) 10 g of dry thin branches and leaves of *Juniperus chinensis* L. var. *sargentii* Henry was immersed in 8- to 10-fold weight of 95% ethanol solvent;

(2) The immersed plant material of step (1) was extracted at a temperature of the boiling point of the solvent for 1 hour, and then filtered with a metal sieve (pore size: 230 mesh) to obtain an extraction solution;

(3) The extraction solution obtained from step (2) was filtered with filter paper [Type: 5A (diameter: 9 cm; pore size: 7 μm; thickness: 0.22 mm); TOYO ROSHI CO., LTD];

(4) The filtrate obtained from step (3) was concentrated to dry by a rotary evaporator to obtain an extract concrete;

(5) The extract concrete obtained from step (4) was mixed with pure water and sonucated to form a suspension.

(6) The suspension obtained from step (5) was lyophilized by liquid nitrogen.

(7) After lyophilization, the product was collected and the product was CBT-143-S.

2. Preparation for Fractional Extract (CBT-143-S-F6F7)

In order to increase the activity of the crude extract, isolation and purification were performed to the crude extract, CBT-143-S. Isolation and purification process are shown in the following, and the preparation process for the fractional extract is shown in FIG. 1

(1) 30 g of CBT-143-S sample was fixed through dry packing (i.e. CBT-143-S was dissolved by an appropriate solvent, and then 2-fold weight (60 g) of silica gel was added thereto. After being mixed well, CBT-143-S was uniformly fixed on the surface of silica gel by a rotary evaporator.) (Step S1);

(2) CBT-143-S sample was isolated through a column which contains 15-fold weight of silica gel to CBT-143-S sample (silica gel was 450 g and filled into a glass column with a diameter of 6 cm. After being filled into the glass column, the silica gel was 28 cm in height, and the dry packing matrix was 4.5 cm in height) (Step S2).

(3) Acetone:n-hexane (1:2) was used as an initial mobile phase to elute the column for 3300 mL, and every 20 mL of elution solution was collected by a tube, fractionally (Step S3) (F1~F7 tube).

(4) The column as washed with acetone (Step S3') (F8 tube);

(5) The column as washed with methanol (Step S3") (F9 tube)

(6) The fractionally collected elution solutions were analyze through normal phase thin layer chromatography, and acetone:n-hexane (2:3) was used as a mobile phase to spread the fractionally collected elution solutions. After being spread, the fractionally collected elution solutions were stained with 10% $H_2SO_{4\,(EtOAc)}$ and heated to 105° C. to color, and $R_f$ values of main color spots therefrom were calculated;

(7) The elution solutions of that $R_f$ values were between 0.35 and 0.55 were collected (Step S4);

(8) The elution solutions mentioned above were combined and concentrated to dry by a rotary evaporator to obtain a fractional extract concrete;

(9) The fractional extract concrete was added to equal weight of pure water, and then sonicated to suspend, and lyophilized by liquid nitrogen; and

(10) After lyophilization, the product, lyophilized powder, was CBT-143-S-F6F7.

3. Isolation, Purification and Identification of Active Ingredient

Figure 2:
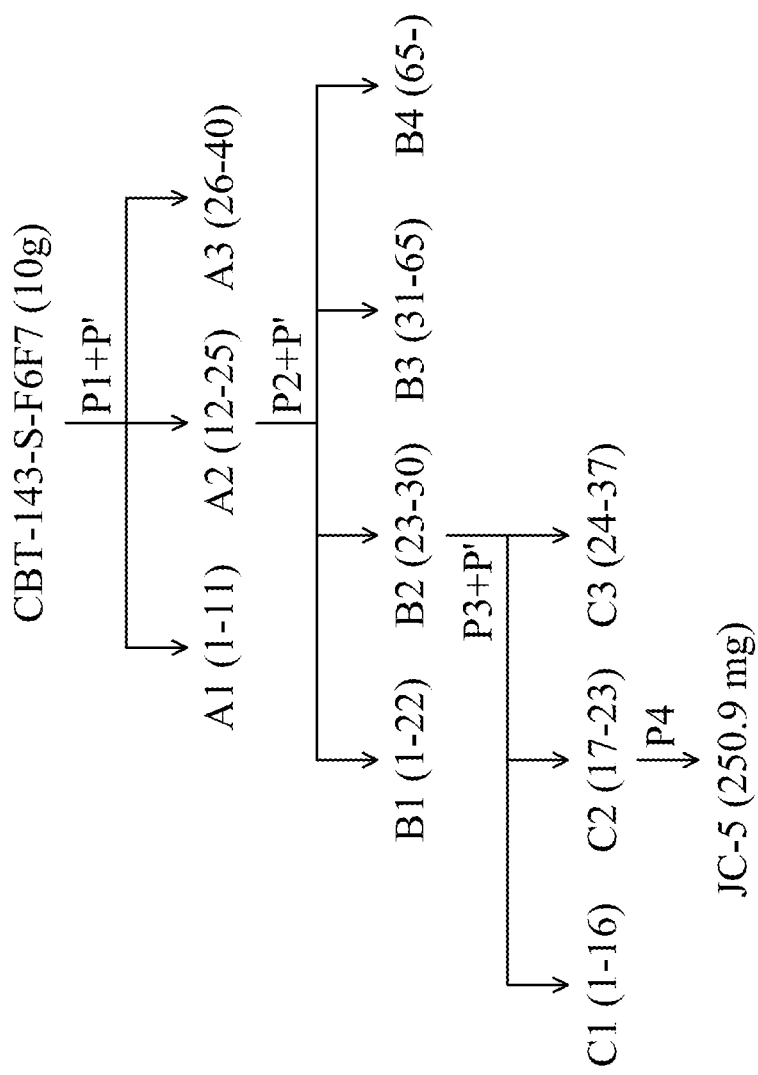
FIG. 2 shows a preparation process for isolating and purifying an active ingredient of the fractional extract, CBT-143-S-F6F7 by column chromatography and activity-directed analysis according to one embodiment of the disclosure.

The active ingredient of the fractional extract, CBT-143-S-F6F7, was isolated and purified by column chromatography and activity-directed analysis. The preparation process is shown in FIG. 2. See FIG. 2. CBT-143-S-F6F7 was used as a raw material, and isolated through a condition P1, and then examined, concentrated and dried through a condition P', and a fraction containing JC-5 active ingredient, CBT-143-S-F6F7-A2, can be obtained thereby. After the fraction was isolated through a condition P2, and then examined, concentrated and dried through a condition P', a fraction containing JC-5 active ingredient, CBT-143-S-F6F7-B2, can be obtained. The fraction CBT-143-S-F6F7-B2 was further isolated through a condition P3, examined, concentrated and dried through a condition P', and then re-crystallized through a condition P4, and a pure substance JC-5 can be obtained thereby. Explanations for conditions P1 to P4 and condition P' is shown in the following:

P1: Flash performance liquid chromatography, FPLC
Column: Silica gel column (0.015~0.040 μm); 2.0 cm (inner diameter)*30 cm (length); Mobile phase: ethyl acetate (EtOAc):n-hexane=1:1; Flow rate: 5 mL/minute; Fraction collector: 10 mL/tube.

P2: Flash performance liquid chromatography, FPLC
Column: Silica gel column (0.015~0.040 μm); 2.0 cm (inner diameter)*30 cm (length); Mobile phase: ethyl acetate (EtOAc):n-hexane=1:1.5; Flow rate: 5 mL/minute; Fraction collector: 10 mL/tube.

P3: Flash performance liquid chromatography, FPLC
Column: Silica gel column (0.015~0.040 μm); 1.5 cm (inner diameter)*30 cm (length); Mobile phase: ethyl acetate (EtOAc):n-hexane=1:1.5; Flow rate: 5 mL/minute; Fraction collector: 10 mL/tube.

P4: Re-crystallizing by methanol

P': Thin layer chromatography, TLC:

A thin layer chromatography aluminum sheet (TLC Silica gel 60 F254, Merck) was cut to 5 cm in length and 7 cm in width, and 1 uL of sample was loaded into the cut aluminum sheet at a position 1 cm from the bottom of the cut aluminum sheet by a quantitative capillary. After the sample was loaded into the cut aluminum sheet and the cut aluminum sheet is dried, the cut aluminum sheet was placed in a spreading tank to spread the sample for 4 cm (spreading solution: ethyl acetate:n-hexane=1:1). After the spreading process was completed and the cut aluminum sheet was dried, a coloring agent (10% $H_2SO_4$ $_{(EtOAc)}$) was spread uniformly on the cut aluminum sheet and heated (105° C. for 5 minutes). After the coloring process was completed, the region containing JC-5 ($R_f$ value: 0.55~0.61, black spot) was observed, and a part of the sample containing the spot was collected and concentrated and dried.

Figure 3A:
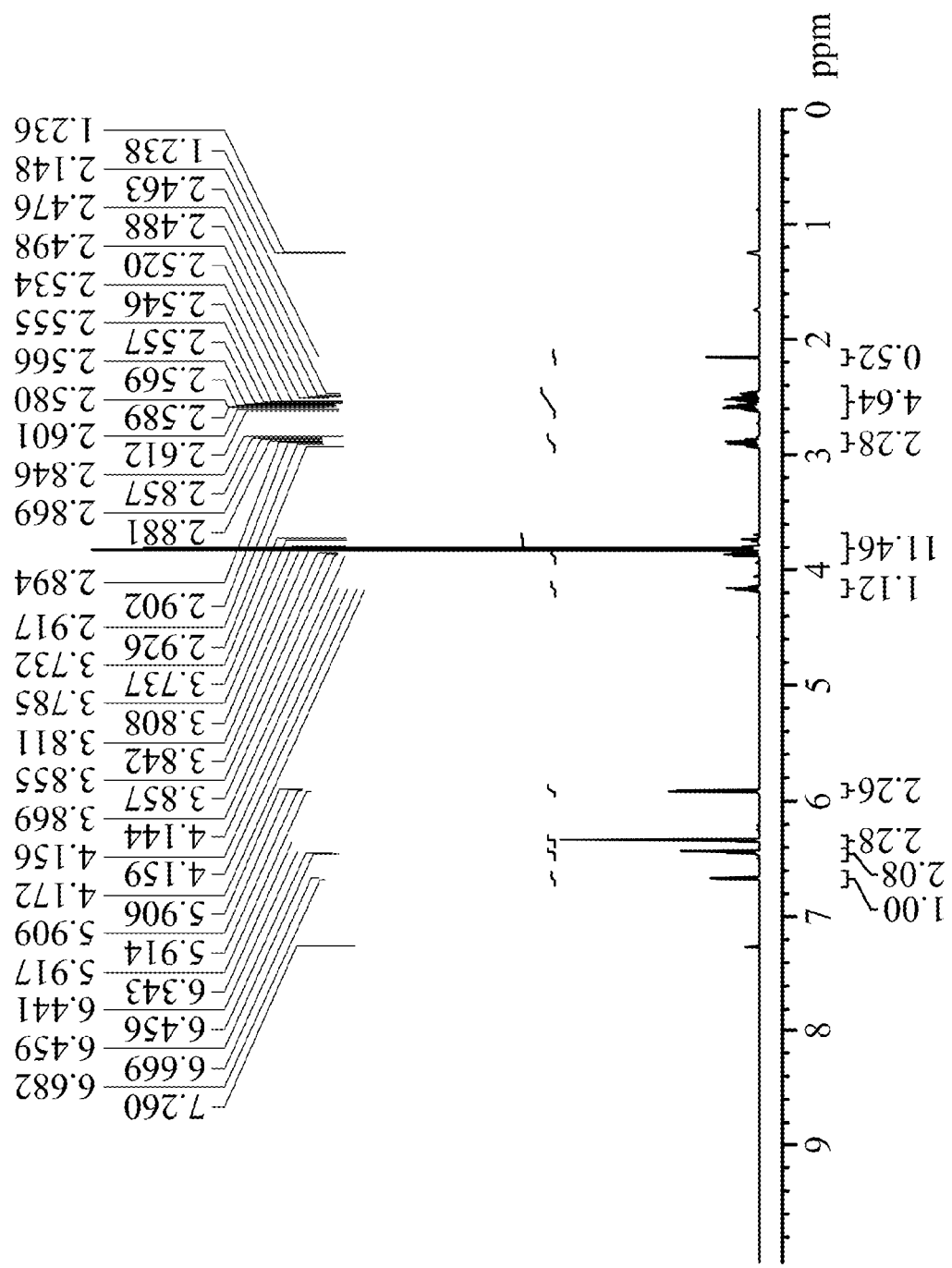
FIG. 3A is a $^1$H NMR spectrum of compound JC-5 according to one embodiment of the disclosure.
Figure 3B:
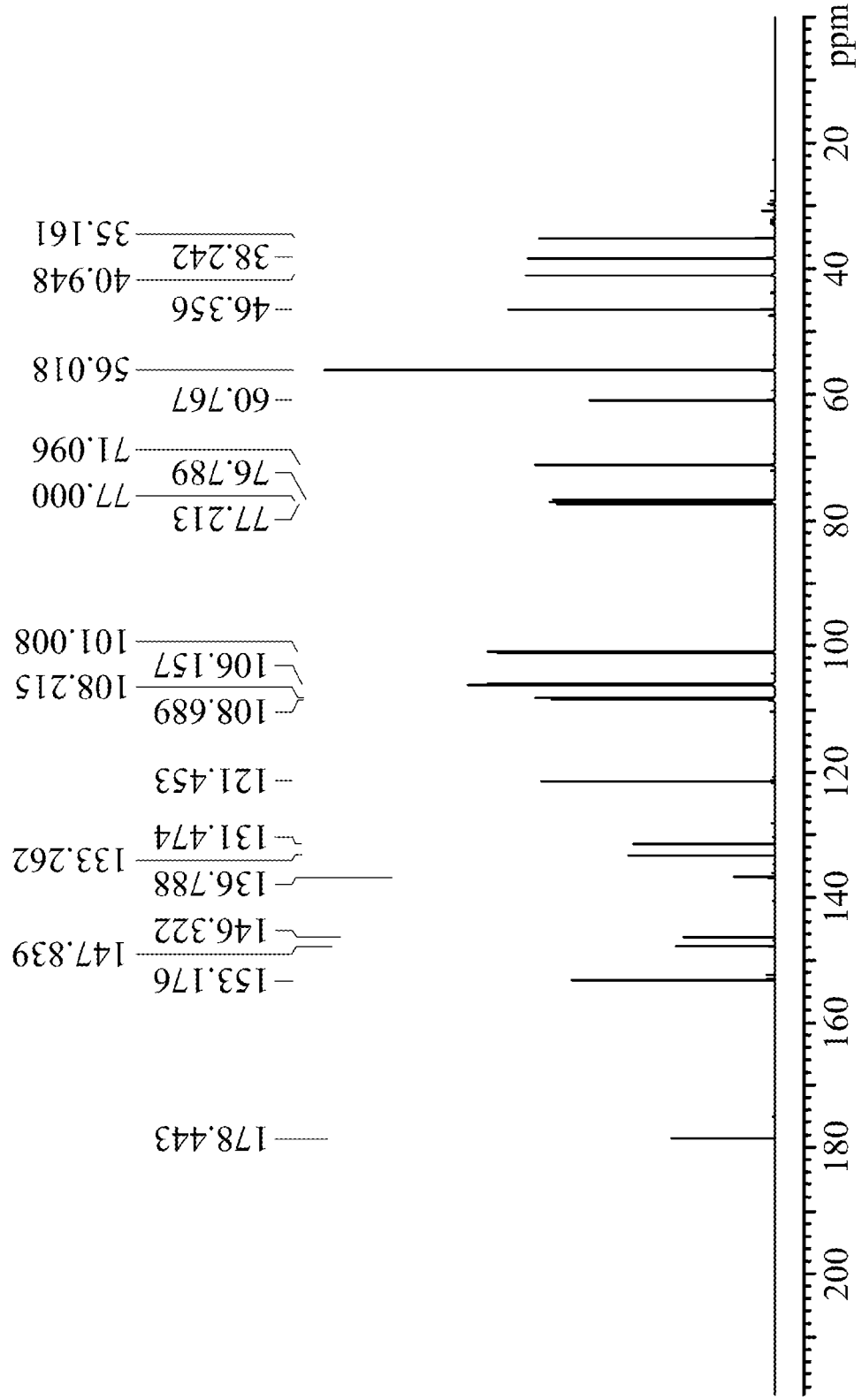
FIG. 3B is a $^{13}$C NMR spectrum of the compound JC-5 according to one embodiment of the disclosure.

The pure substance, JC-5, was identified by nuclear magnetic resonance spectroscopy, NMR. The results are shown in FIGS. 3A and 3B. FIG. 3A is a $^1H$ NMR spectrum of compound JC-5, and this spectrum shows the number of hydrogen atoms which contained by the structure of the compound JC-5. According to the positions occurring hydrogen atoms (δ value) and ratio of integral values, it could be extrapolated that there were a total of 24 hydrogen atoms in the structure. FIG. 3B is a $^{13}C$ NMR spectrum of the compound JC-5, and this spectrum shows that there are a total of 22 carbon atoms in the structure of the compound JC-5.

Figure 4:
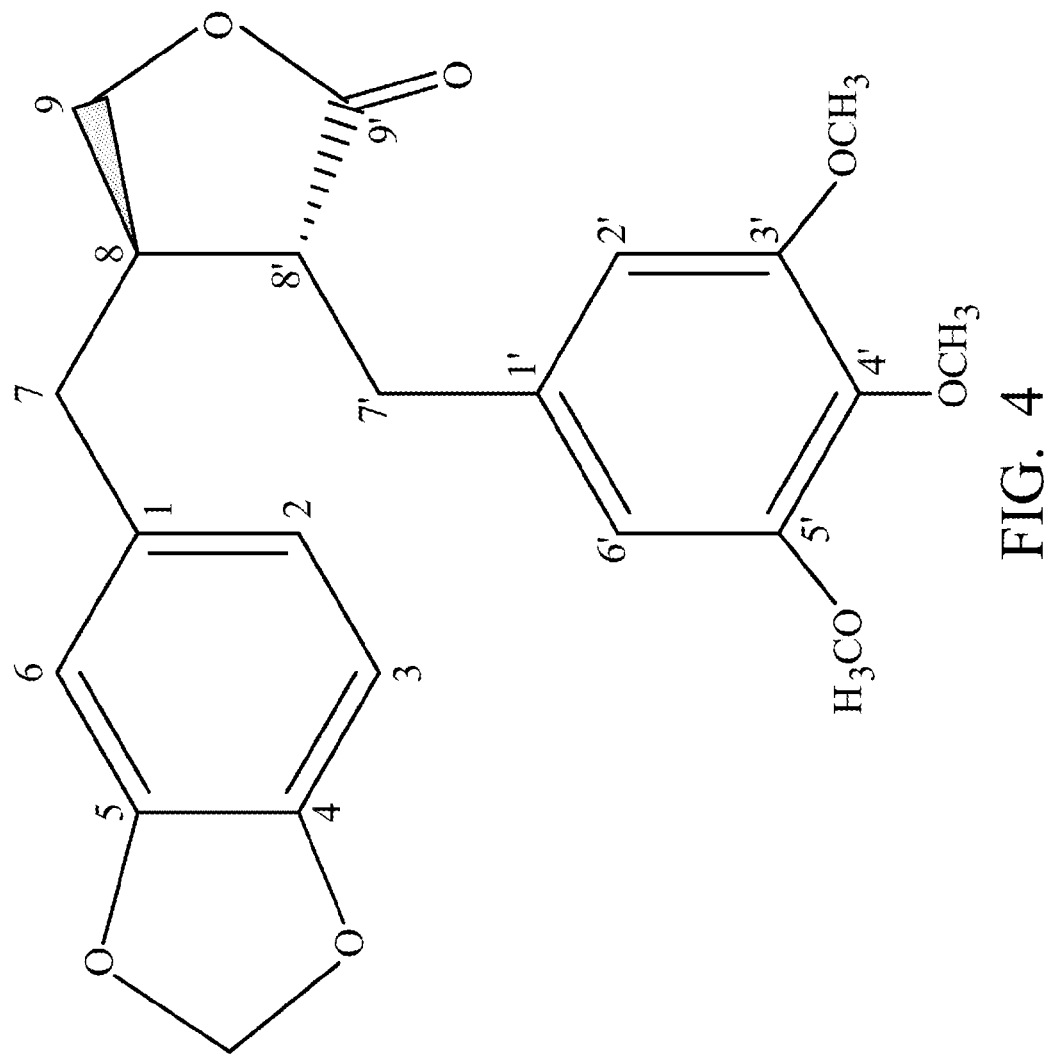
FIG. 4 shows the structure of yatein according to one embodiment of the disclosure.

The data obtained from FIG. 3A and FIG. 3B were compared with the description related to yatein of the literature [Ikeda, R.; Nagao, T.; Okabe, H.; Nakano, Y.; Matsunaga, H.; Katano, M.; Mori, M. Chem. Pharm. Bull. 1998, 46, 871-874.], and the data are sorted in Table 2. According to the comparison result mentioned above, the compound JC-5 was identified as yatein. Moreover, the structure of yatein is shown in FIG. 4.

TABLE 2

Distribution of the hydrogen atoms and carbon atoms contained in the structure of yatein

| Position | Data from the experiment (600 MHz, $CDCl_3$) | |
|---|---|---|
| | C | H (J in Hz) |
| 1 | 131.47 | |
| 2 | 121.45 | 6.45, dd(7.8, 1.8) |
| 3 | 108.21 | 6.68 d(7.8) |
| 4 | 146.32 | |
| 5 | 147.83 | |
| 6 | 108.68 | 6.44 d(1.8) |
| 7 | 38.24 | 2.56, m |
| | | 2.56, m |
| 8 | 40.94 | 2.47, m |
| 9 | 71.09 | 4.15, t(9.6); |
| | | 3.85, t(8.4) |
| 1' | 133.26 | |
| 2' | 106.15 | 6.34, s |
| 3' | 153.17 | |
| 4' | 136.78 | |
| 5' | 153.17 | |
| 6' | 106.15 | 6.34, s |
| 7' | 35.16 | 2.91, dd(14.4, 5.4); |
| | | 2.86, dd(14.4, 5.4) |
| 8' | 46.35 | 2.58, m |
| 9' | 178.44 | |
| $OCH_2O$ | 101.00 | 5.90, d(1.8); |
| | | 5.91, d(1.8) |
| C-3', $OCH_3$ | 56.01 | 3.81, s |
| C-4', $OCH_3$ | 60.76 | 3.80, s |
| C-5', $OCH_3$ | 56.01 | 3.81, s |

Furthermore, by using Matrigel (BD, Cat. No. 356231) as a matrix and observing the state of human umbilical vein endothelial cells (HUVECs) constructing a net structure on the matrix, state of JC-5 (yatein) inhibiting the formation of HUVEC net structure was analyzed. Analysis standards and conditions are described in the following. The total length of the net structure was calculated through NIS element image analysis software (Nikon; Agent: Lin Trading Co., Ltd. Taiwan), wherein by using the total length of a net structure formed from a group without a drug addition as 100%, the state of JC-5 inhibiting the formation of HUVEC net structure was analyzed.

Figure 5:
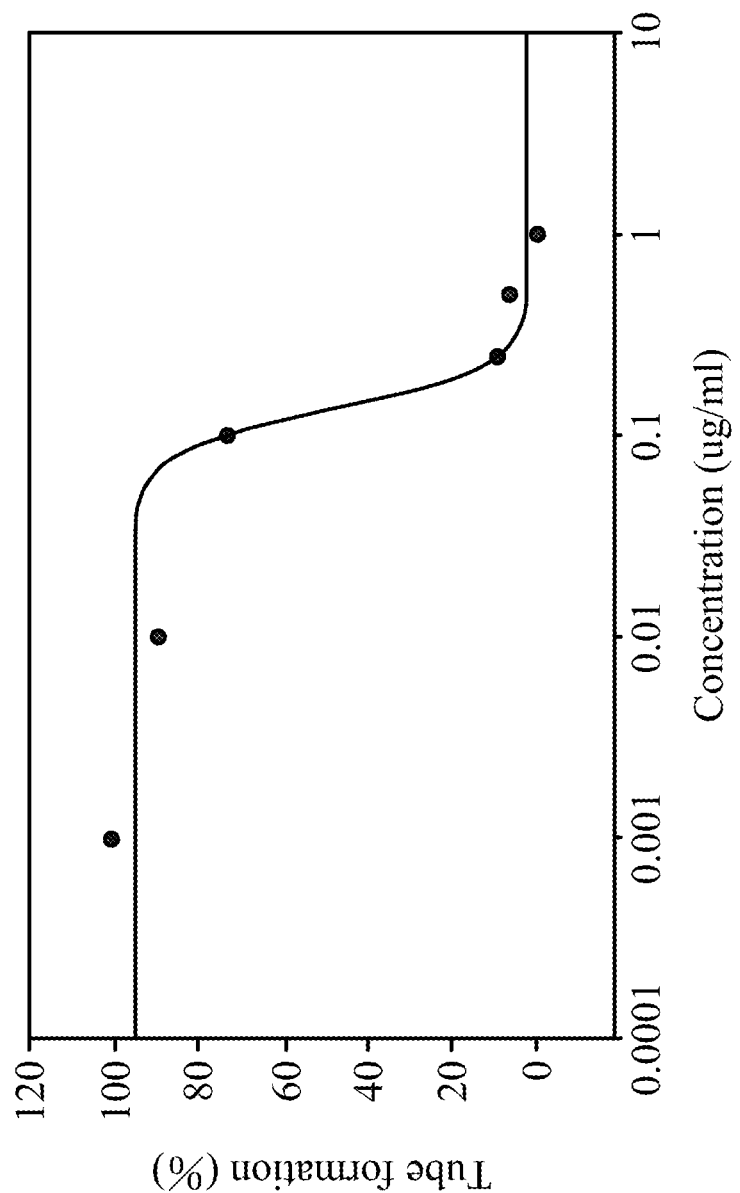
FIG. 5 shows activity analysis results for JC-5, yatein, inhibiting formation of net structure according to one embodiment of the disclosure.

According to activity analysis results for of inhibiting the formation of net structure as mentioned above, it was found that 50% inhibiting concentration ($IC_{50}$) of yatein for inhibiting tube formation was 0.335 μM (FIG. 5). Therefore, yatein was determined to be an active ingredient.

4. High-Performance Liquid Chromatography (HPLC) Fingerprint of the Crude Extract (CBT-143-S) and the Fractional Extract (CBT-143-S-F6F7)

Analysis Method:

Sample preparation: 10 mg of powder of CBT-143-S and 10 mg of powder of CBT-143-S-F6F7 were placed in respective 10 mL volumetric flasks. After that, 95% ethanol was added to the 10 mL volumetric flasks to quantify the volume to 10 mL, and the 10 mL volumetric flasks were sonicated to completely dissolve the powder therein.

Conditions for high-performance liquid chromatography:

Type of chromatography column: Cosmosil 5C18-MS-II 4.6*250;

Flow rate: 0.8 ml/minute;

Observation wave length: 280 nm;

Mobile phase: A: 0.1% $H_3PO_4$; B: $CH_3CN$; C: MeOH;

Gradient: A/B/C=65/25/10 (60 minutes)→A/B/C=25/60/15 (1 minute)→A/B/C=65/25/10 (9 minutes).

Figure 6A:
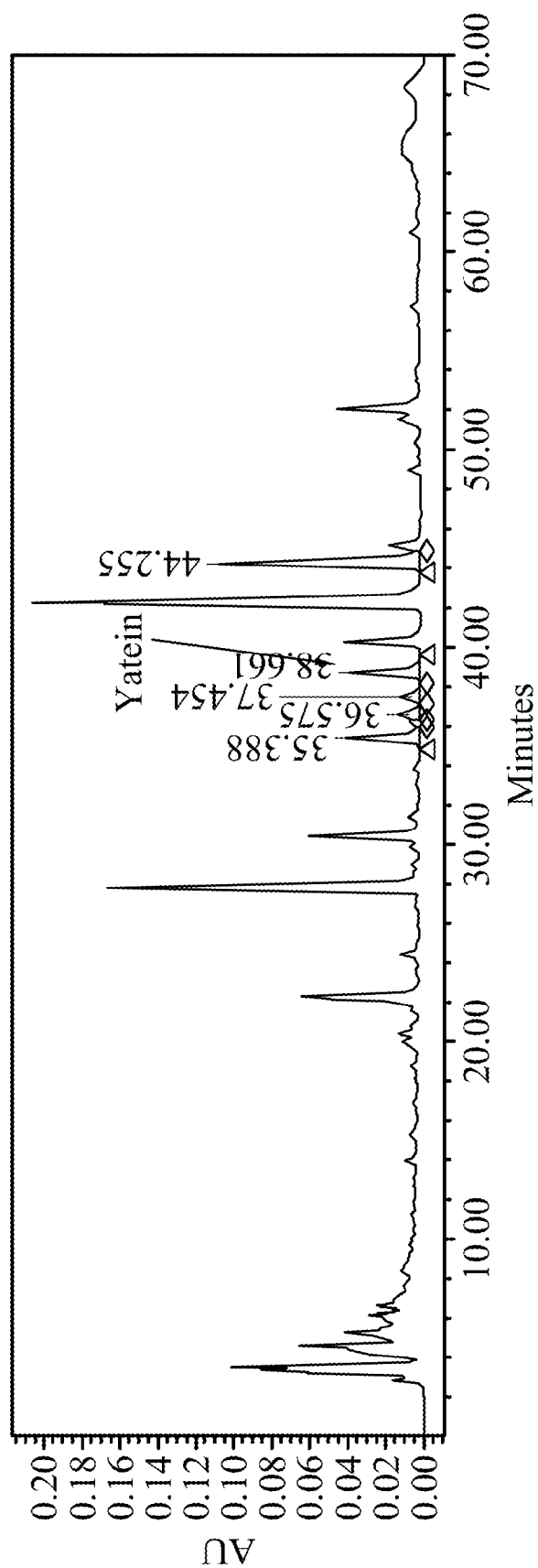
FIG. 6A shows the high-performance liquid chromatography fingerprint of the crude extract, CBT-143-S according to one embodiment of the disclosure.
Figure 6B:
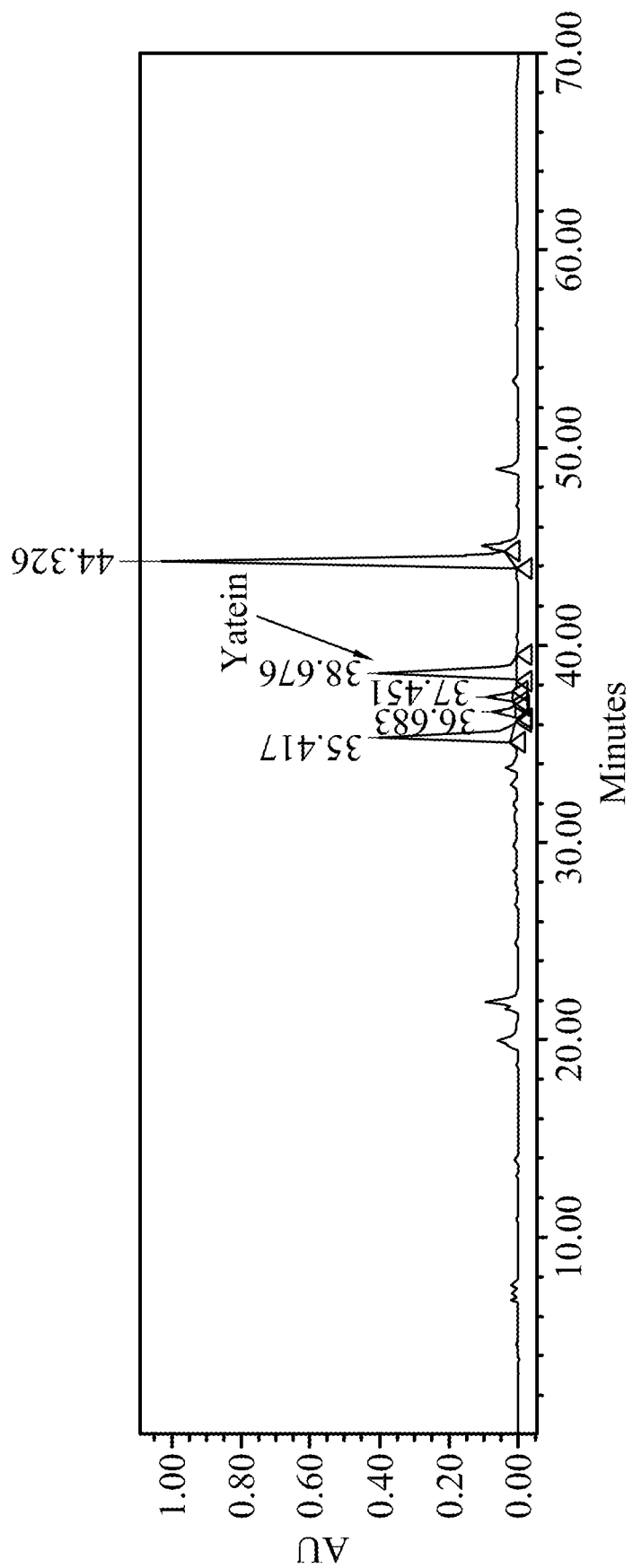
FIG. 6B shows the high-performance liquid chromatography fingerprint of the fractional extract, CBT-143-S-F6F7 according to one embodiment of the disclosure.

Analysis Results:

FIG. 6A and FIG. 6B show the high-performance liquid chromatography graphs for quality control analysis for the crude extract (CBT-143-S) and the fractional extract (CBT-143-S-F6F7), respectively, and can used as a reference for quality control of the extract of the present disclosure.

Figure 6C:
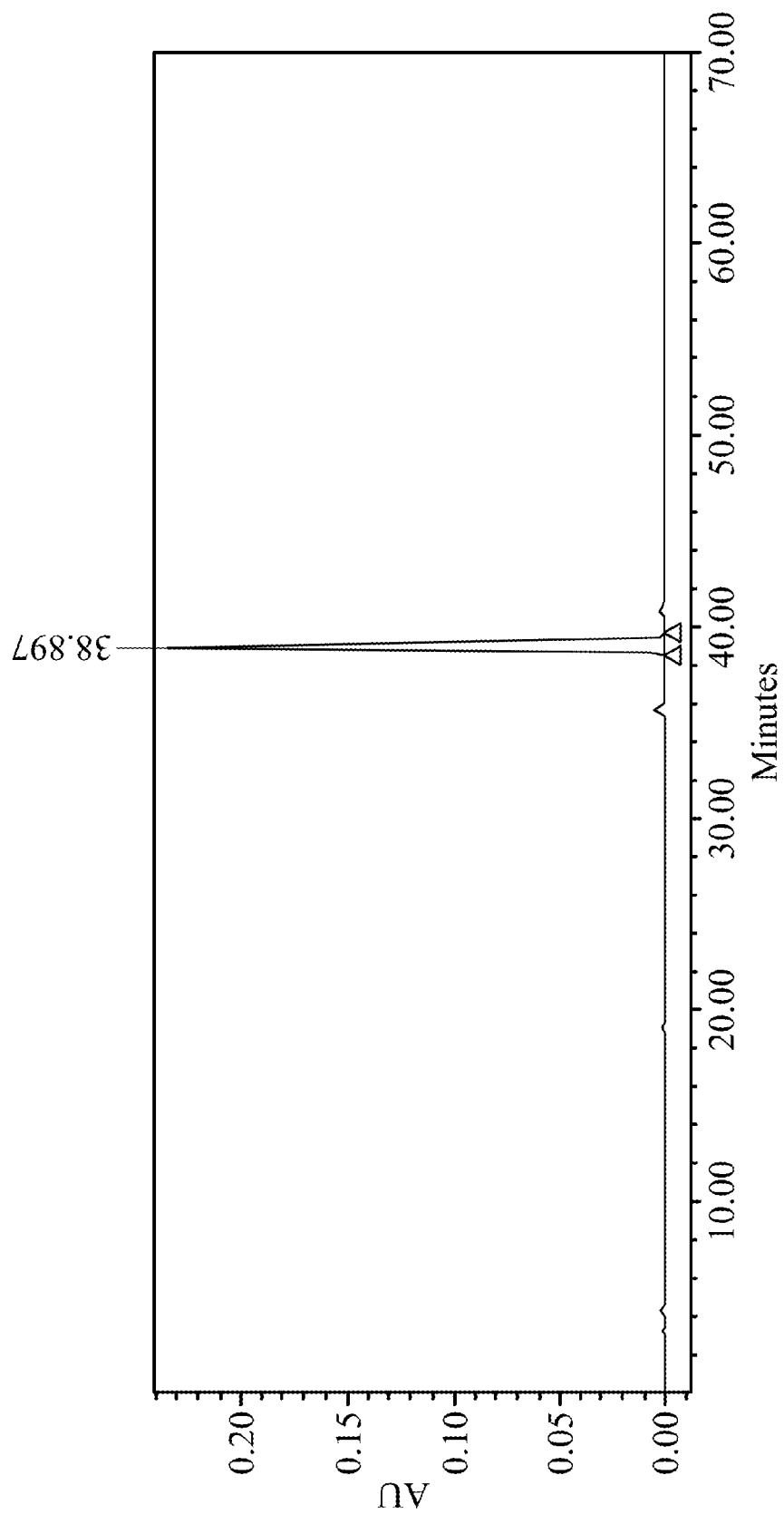
FIG. 6C shows the high-performance liquid chromatography fingerprint of the yatein control standard according to one embodiment of the disclosure.

By using the purified yatein (JC-5) pure substance as a control standard, high-performance liquid chromatography qualitative/quantitative analysis methods for the crude extract (CBT-143-S) and the fractional extract (CBT-143-S-F6F7) were developed, and the high-performance liquid chromatography graphs for the crude extract (CBT-143-S) and the fractional extract (CBT-143-S-F6F7) were compared with the high-performance liquid chromatography fingerprint of the yatein control standard (see FIG. 6C), respectively. According to FIG. 6A and FIG. 6B, the high-performance liquid chromatography graphs for the crude extract (CBT-143-S) and the fractional extract (CBT-143-S-F6F7) all present a main peak for the JC-5 active ingredient. In addition, the extracts of thin branches and leaves of *Juni-*

*perus chinensis* L. var. *sargentii* Henry extracted by different solvents were also analyzed, and the yatein contents thereof are shown in above Table 1.

5. In vitro Evaluation for Activities of the Crude Extract (CBT-143-S) and the Fractional Extract (CBT-143-S-F6F7)

(1) Inhibition of Blood Vessel Tube Formation

By using Matrigel (BD, Cat. No. 356231) as a matrix and observing the state of human umbilical vein endothelial cells (HUVECs) constructing a net structure on the matrix, the states of the crude extract (CBT-143-S) and the fractional extract (CBT-143-S-F6F7) inhibiting the formation of HUVEC net structure were analyzed. The analysis standards and conditions are described in the following. The total length of the net structure was calculated through NIS element image analysis software (Nikon; Agent: Lin Trading Co., Ltd. Taiwan), wherein by using the total length of a net structure formed from a group without a drug addition as 100%, the states of the crude extract (CBT-143-S) and the fractional extract (CBT-143-S-F6F7) inhibiting the formation of HUVEC net structure was analyzed.

Figure 7:
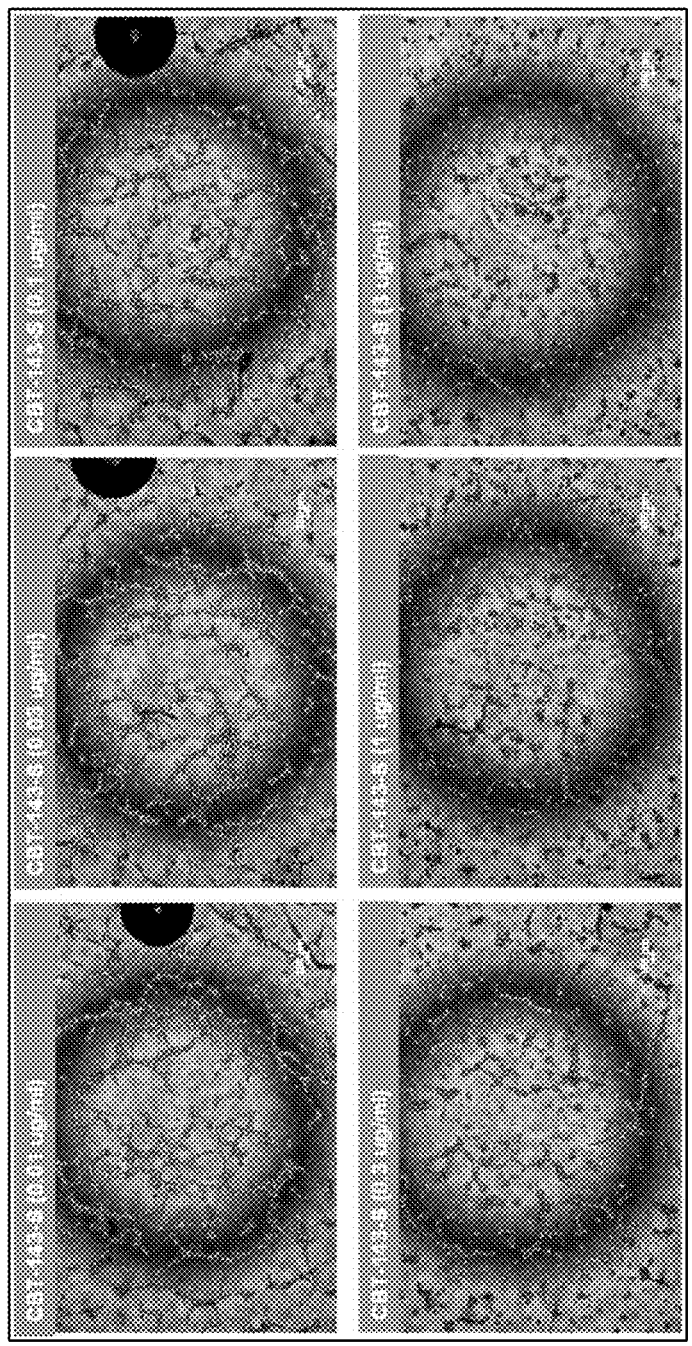
FIG. 7 shows the state of the crude extract, CBT-143-S, inhibiting the formation of HUVEC net structure according to one embodiment of the disclosure.
Figure 8:
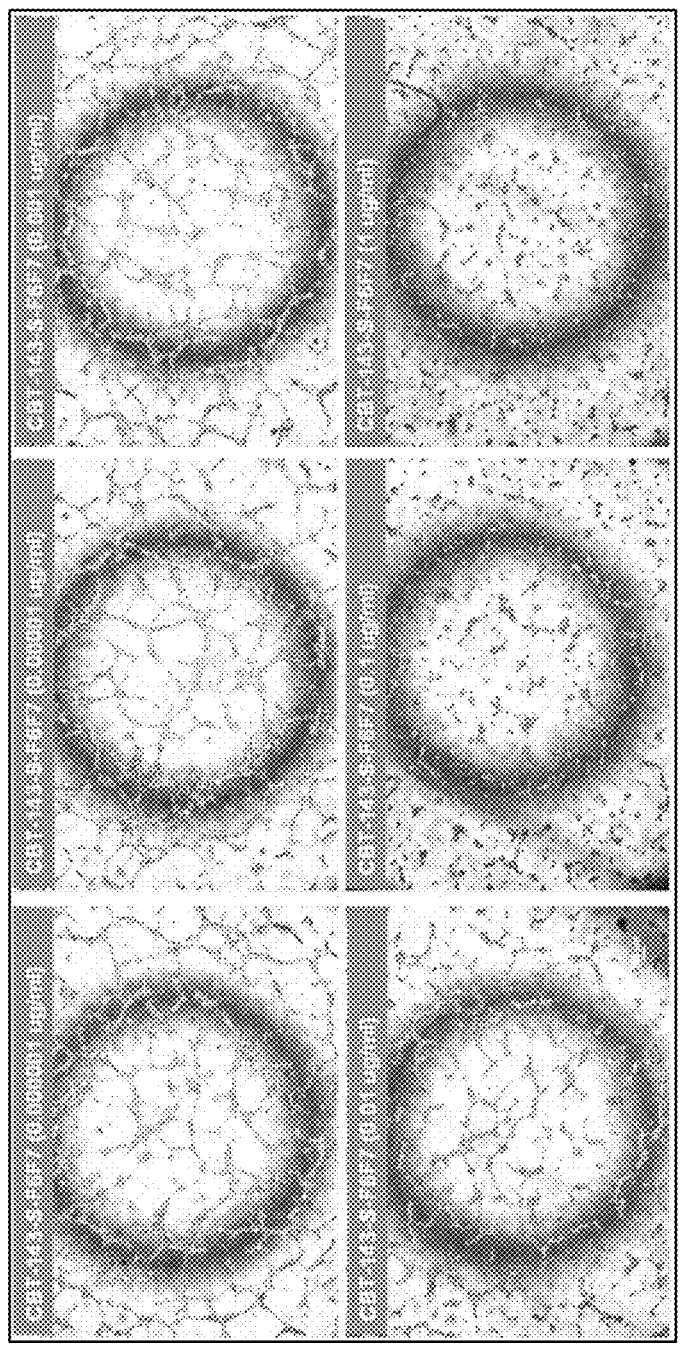
FIG. 8 shows the state of the fractional extract, CBT-143-S-F6F7, inhibiting the formation of HUVEC net structure according to one embodiment of the disclosure.

The experimental results showed that by increasing the testing concentration, the inhibition effects of the crude extract (CBT-143-S) and the fractional extract (CBT-143-S-F6F7) on tube formation were also increased, and those showed significant dose-dependent effects (FIG. 7 and FIG. 8).

Figure 9:
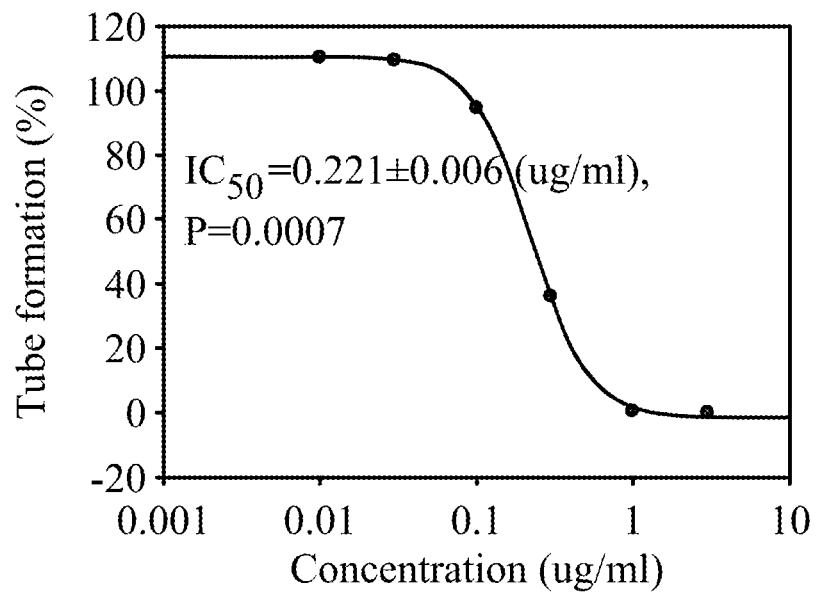
FIG. 9 shows the relative relationship between the concentration of the crude extract, CBT-143-S, and the tube formation for HUVECs according to one embodiment of the disclosure.
Figure 10:
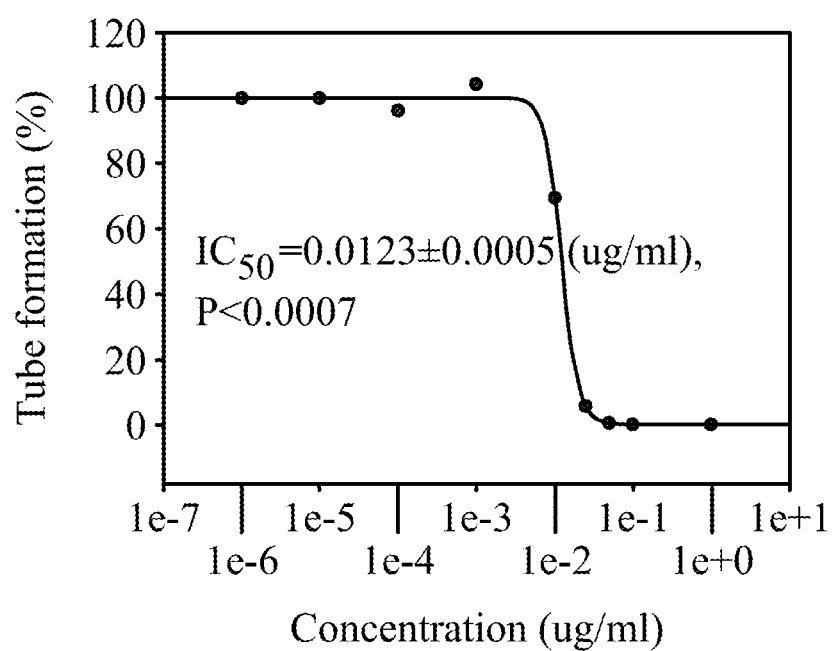
FIG. 10 shows the relative relationship between the concentration of the fractional extract, CBT-143-S-F6F7, and the tube formation for HUVECs according to one embodiment of the disclosure.
Figure 11:
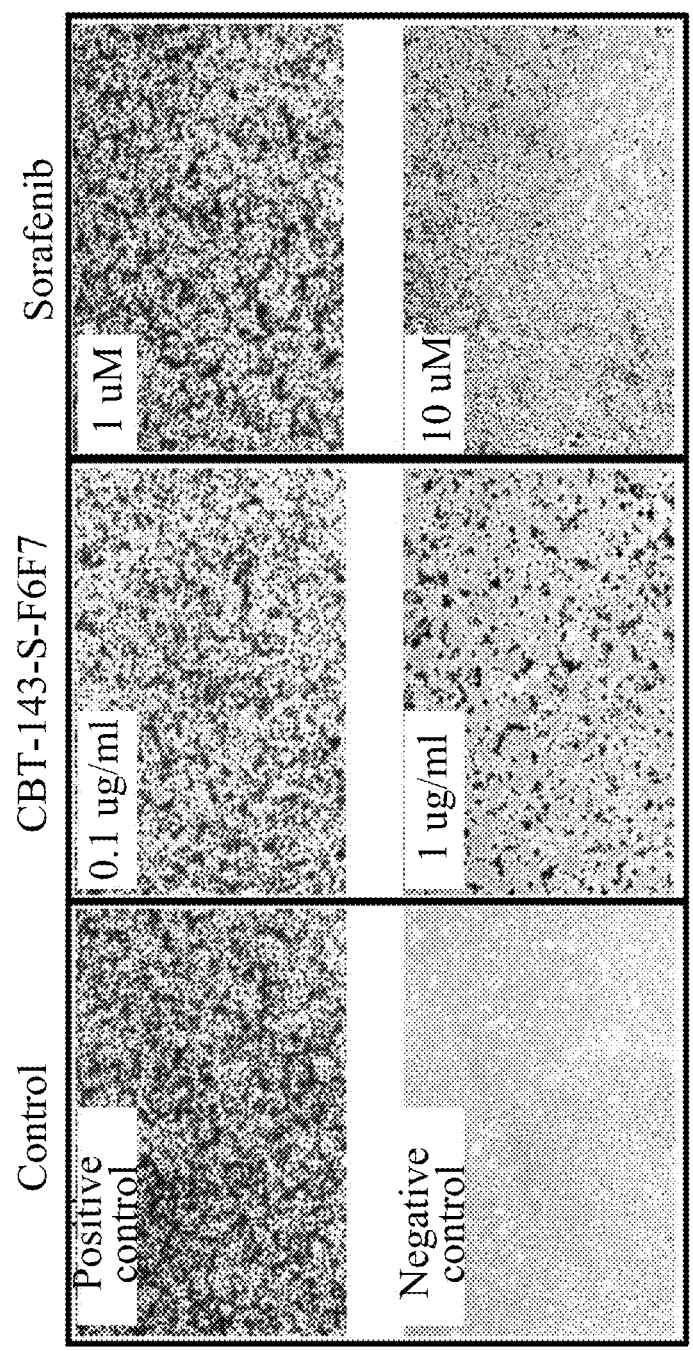
FIG. 11 shows the effect of the fractional extract, CBT-143-S-F6F7 on the mobility of HUVECs according to one embodiment of the disclosure.

Furthermore, after calculation, it was determined that 50% inhibiting concentrations ($IC_{50}$) of the crude extract (CBT-143-S) and the fractional extract (CBT-143-S-F6F7) for inhibiting tube formation were 0.221 μg/mL and 0.0123 μg/mL (FIG. 9 and FIG. 10). The results showed that through a purification process, the activity of the fractional extract (CBT-143-S-F6F7) could be increased 20.3-fold, compared with that of the crude extract (CBT-143-S).

(2) Evaluation for Inhibition of Mobility of Vascular Endothelial Cells (HUVEC Migration Assay)

In a BD transwell system, the state of HUVEC migrating downward to pass through the membrane in the presence of nutrition for driving HUVEC was observed. By using a group without serum for driving as a negative control and using a group with serum for driving as a positive control, the state of the extract inhibiting migration of the endothelial cells, wherein the cells stained by crystal violet allowed the migration thereof to be easily observed. The results showed that the fractional extract (CBT-143-S-F6F7) was indeed capable of inhibiting migration of the endothelial cells.

(3) Evaluation for Inhibition of Mobility of Hepatocellular Carcinoma Cells (Wound Healing Migration Assay)

Figure 12:
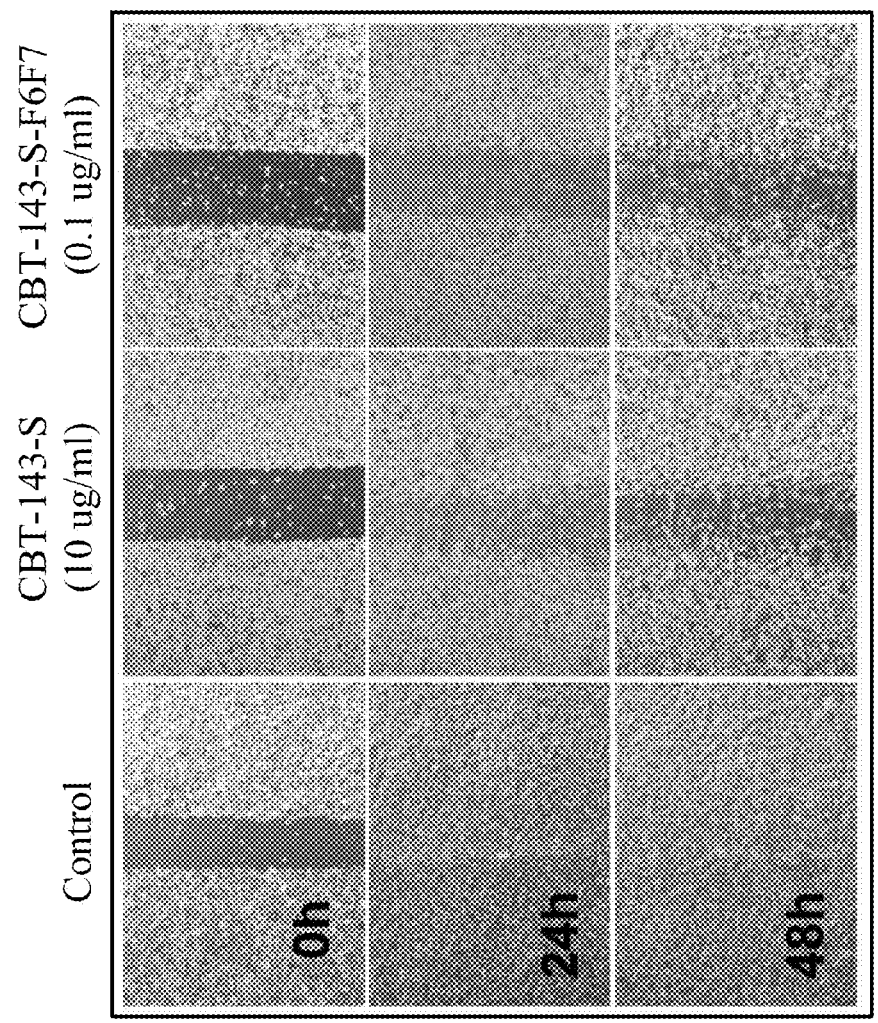
FIG. 12 shows the effects of the crude extract, CBT-143-S, and the fractional extract, CBT-143-S-F6F7, on the mobility of SK-Hep-1 cells according to one embodiment of the disclosure.

Hepatocellular carcinoma cell line, SK-Hep-1, which has high mobility, was selected to be tested. First, the cells were inoculated in a 6-well plate. After attaching to the plate, a part of the cells were scraped to form a line on the plate. After the cells scraped from the line were washed out, the state of the cells migrating to mend the line was observed at 24 hours and 48 hours (FIG. 12). The results showed that, after treatment with different concentrations of the crude extract (CBT-143-S) and the fractional extract (CBT-143-S-F6F7), the cell migration of the cells were all reduced.

At 48 hours, the observation was terminated, and an MTT assay was immediately performed on the cells in the plate to determine the viability of the cells. Through comparing the cell mobility with cell viability, it could be determined whether the crude extract (CBT-143-S) and the fractional extract (CBT-143-S-F6F7) had the effect of inhibiting migration of SK-Hep-1.

According to the results of the analysis, it was determined that the effect of inhibiting migration of SK-Hep-1 of the crude extract (CBT-143-S) and the fractional extract (CBT-143-S-F6F7) increased with time.

6. In vivo Anti-Angiogenesis Experiments for the Crude Extract (CBT-143-S) and the Fractional Extract (CBT-143-S-F6F7)

Through a subcutaneous injection to BALB/c mice to form Matrigel plugs, an evaluation was made of whether a test substance was capable of inhibiting angiogenesis induced by vascular endothelial growth factor or Hep-3B conditional medium (CM).

(1) Matrigel Plugs Assay

Matrigel is extracted from the Engelbreth-Holm-Swarm (EHS) mouse sarcoma and contains rich extracellular matrix proteins and contains various factors need by vascular growth. In a condition of room temperature and 37° C., Matrigel is capable of polymerize as a solid gel from, and can provide a better growth environment for vascular endothelial cells.

Matrigel and vascular endothelial growth factors (FGFb+VEGF) or Hep-3B conditional medium (CM) were mixed, and then a test substance was added thereto and mixed.

The experimental method is described as follows:

(a) Animal strain: Female BALB/c mice (BALB/cAnNCrlBltw, purchased from BioLasco Taiwan Co., Ltd), 6-8 weeks old.

(b) A group treated with Matrigel mixed with PBS was used as a negative control group, and a group treated with Matrigel mixed with FGFb (500 ng/ml)+VEGF (500 ng/ml) or mixed with Hep-3B conditional medium (CM) was used as a positive control group. A test substance was mixed with Matrigel containing vascular endothelial growth factors and then injected to BALB/c mice by subcutaneous injection to observe whether the test substance is capable of inhibiting angiogenesis in a Matrigel.

(c) Hemoglobin content in Matrigel was quantified by a QuantiChrom™ Hemoglobin Assay Kit (DIHB-250) to evaluate the amount of neo-blood vessels in Matrigel.

After subcutaneous injection to BALB/c mice for 14 days, the Matrigel plugs in the subcutaneous tissue of the mouse was taken out and equal amount of dispase was added therein to form a mixture and reacted at 37° C. for 16 hours to dissolve intercellular substance gel. After that, the mixture was centrifuged at 14,000 rpm for 10 minutes, and transferred the supernatant to another microcentrifuge tube. 50 μL of supernatant and 200 μL of reaction reagent contained by the Hemoglobin Assay Kit are mixed. After the supernatant was reacted with the reagent for 5 minutes, the optical density (O.D.) at 400 nm therefrom was determined. Optical density (O.D.) values were converted into a unit concentration according to the formula shown in the following:

$$((OD_{Sample} - OD_{Blank})/(OD_{Calibration} - OD_{Blank})) \times 100 \times n \text{ (mg/dL)},$$

wherein 100 was a calibrator concentration, and n is dilution-fold.

The Experimental Results:

(a) Assay for Evaluation of In Vivo Growth Factor-Induced Angiogenesis

In the assay for evaluation of in vivo growth factor induced angiogenesis, in the negative control group which was only treated with PBS, the hemoglobin concentration of the Matrigel plug implanted in the subcutaneous tissue of the mouse for 14 days was close to a background value, 17.68±11.64 (mg/dL). However, after addition of FGFb (500 ng/ml)+VEGF (500 ng/mL), significant angiogenesis could be found in the Matrigel plug, and the hemoglobin concentration could reach 52.64±26.18 (mg/dL). In the group orally administered with Nexavar every day (30 mg/kg/day), the hemoglobin concentration was significantly reduced to 27.09±5.88 (mg/dL). In the group treated with the crude extract (CBT-143-S) (100 µg/mL), the hemoglobin concentration was 27.92±9.62 (mg/dL). Moreover, in the groups treated with 30 µg/mL and 100 µg/mL of the fractional extract (CBT-143-S-F6F7), the hemoglobin concentrations were 56.70±5.58 (mg/dL) and 25.08±9.59 (mg/dL), respectively.

Figure 13:
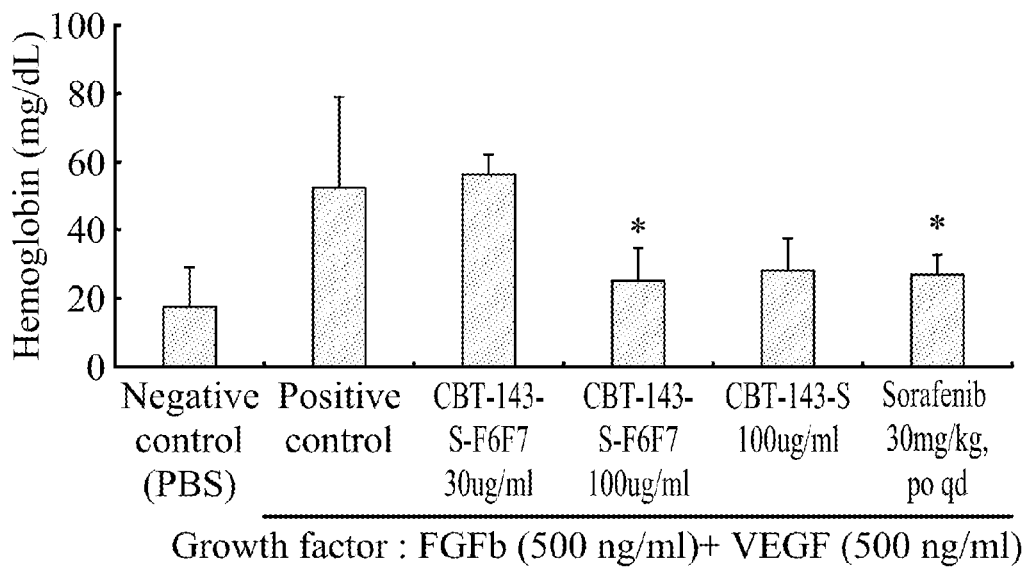
FIG. 13 shows the effects of the crude extract, CBT-143-S, and the fractional extract, CBT-143-S-F6F7, on in vivo growth factor-induced angiogenesis. Data are represented by mean±standard deviation; p<0.05:* (compared with the growth factor treatment group) according to one embodiment of the disclosure.

The results showed that at a higher concentration, the crude extract (CBT-143-S) and the fractional extract (CBT-143-S-F6F7) have the potential for inhibiting angiogenesis (FIG. 13).

(b) Assay for Evaluation of In Vivo Hep-3B Hepatocellular Carcinoma Cell Conditional Medium-Induced Angiogenesis In the assay for evaluation of in vivo Hep-3B hepatocellular carcinoma cell conditional medium-induced angiogenesis: in the negative control group, which was only treated with PBS, the hemoglobin concentration of the Matrigel plug implanted in the subcutaneous tissue of the mouse for 14 days was 16.23±11.64 (mg/dL). However, after the addition of a conditional medium, significant angiogenesis could be found in the Matrigel plug, and the hemoglobin concentration could reach 52.61±13.14 (mg/dL). In the group orally administered with Nexavar every day (30 mg/kg/day), the hemoglobin concentration was significantly reduced to 25.05±17.59 (mg/dL). In the group treated with the crude extract (CBT-143-S) (100 µg/mL), the hemoglobin concentration was 22.91±15.95 (mg/dL). Moreover, in the groups respectively treated with 30 µg/mL and 100 µg/mL of the fractional extract (CBT-143-S-F6F7), the hemoglobin concentrations were 51.49±8.97 (mg/dL) and 20.61±7.52 (mg/dL), respectively.

Figure 14:
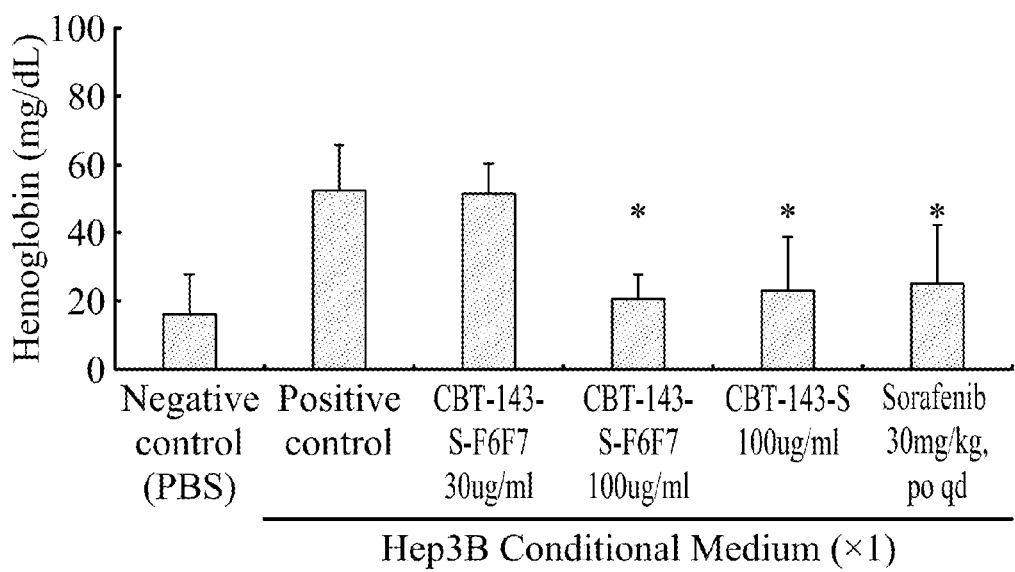
FIG. 14 shows the effects of the crude extract, CBT-143-S, and the fractional extract, CBT-143-S-F6F7, on in vivo cell conditional medium-induced angiogenesis. Data are represented by mean±standard deviation; p<0.05:* (compared with the conditional medium treatment group) according to one embodiment of the disclosure.

The results showed that at a higher concentration, the crude extract (CBT-143-S) and the fractional extract (CBT-143-S-F6F7) have the potential for inhibiting angiogenesis (FIG. 14).

(2) In Vivo Anti-Angiogenesis Experiment (Chorioallantoic Membrane (CAM) Assay)

Filter paper absorbed a test drug or PBS, and then was placed on a chorioallantoic membrane (CAM) of a chicken embryo, and vascular formation was observed.

The chicken embryo of a specific-pathogen-free (SPF) White Leghorn chicken was placed laterally in an incubator (37.3° C., RH 55-60%). On day 4 (D4) of the incubation period, 2.5 mL of albumin was sucked out with a 20 G needle and a fake air chamber was made on the embryo. After that, the needle hole and the fake air chamber were sealed with 3M breathable tape. On day 7, a test drug was dissolved with DMSO and then diluted with PBS. For each group, including a PBS control group, the DMSO final concentration was 1%. Circular Advantec® Filter paper (diameter: 6 mm) (Toyo Roshi Kaisha, Ltd.) was used to absorb the diluted test drug, and the absorbing volume was 25 µL. Each test drug was prepared for 3 dosages, which were 50, 25, and 10 µg/embryo. Moreover, on day 7 (D7), the filter paper was placed on a chorioallantoic membrane, and then on day 9 (D9), the chorioallantoic membrane was photographed with a dissecting microscope, SZX16 (Olympus) at 1.25× objective lens. By using the filter paper as the center, 4 concentric circles were marked on the photograph (the diameters thereof were 7, 8, 9 and 10 mm; the total circumference of the four concentric circles was 106.8 mm, and the total circumference represented the region close to the filter paper. The amount of vessel crossed with the concentric circles (namely, the vascular density index, or VDI) was determined by the naked eye) to evaluate the state of angiogenesis. The vascular density index for the same photograph was determined by 3 people and the mean value thereof was adopted. The vascular density index for each drug treatment group was compared with the control group to observe whether there was a significant difference or not. An unusual region for vascular morphology was observed and photographed using 4× and 8× objective lenses.

Figure 15:
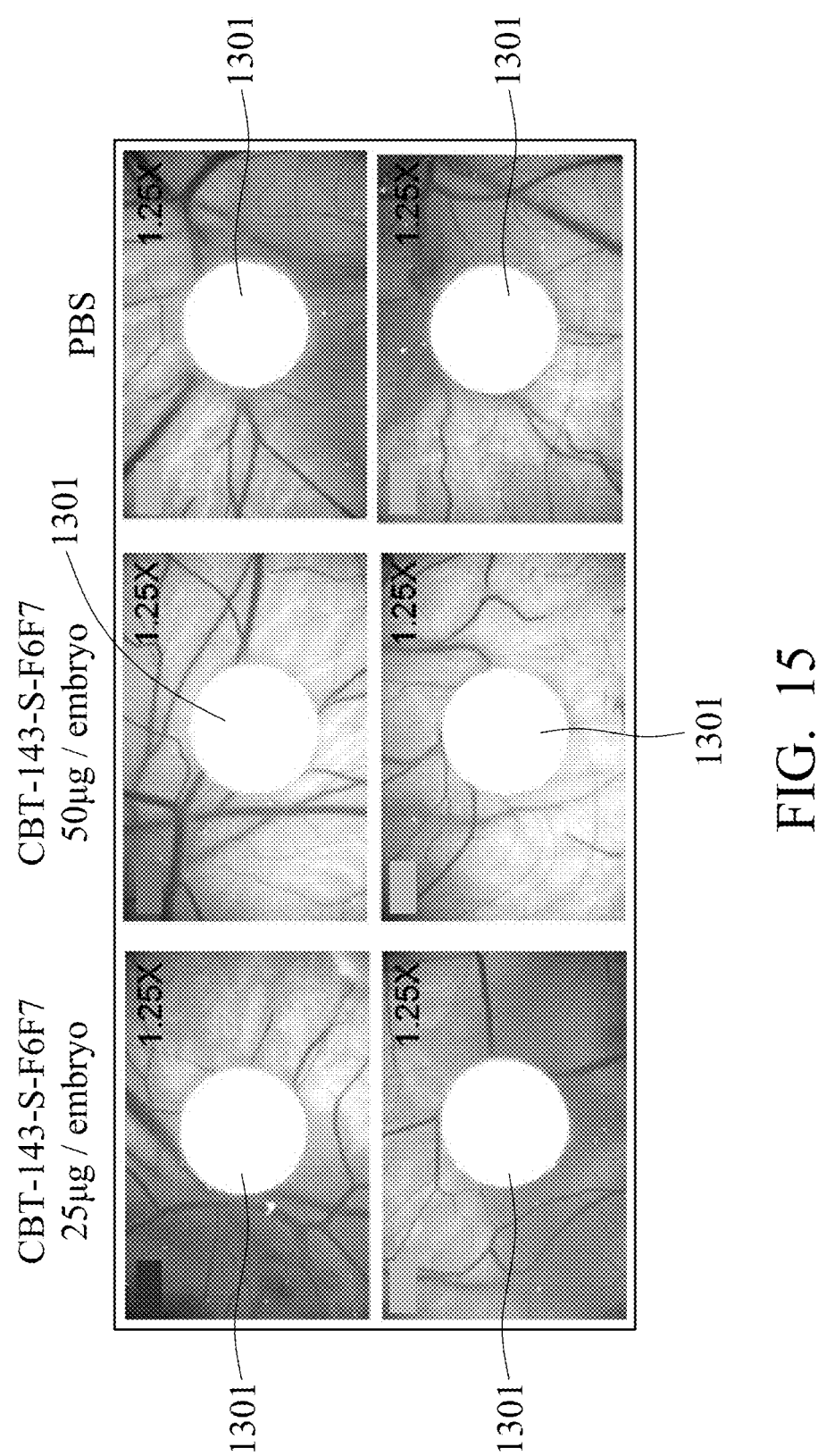
FIG. 15 shows the effects of the fractional extract, CBT-143-S-F6F7, and the crude extract, CBT-143-S, on angiogenesis in a living body (1.25× magnification). Reference number 1301 in FIG. 15 refers to filter paper containing a test drug according to one embodiment of the disclosure.
Figure 16:
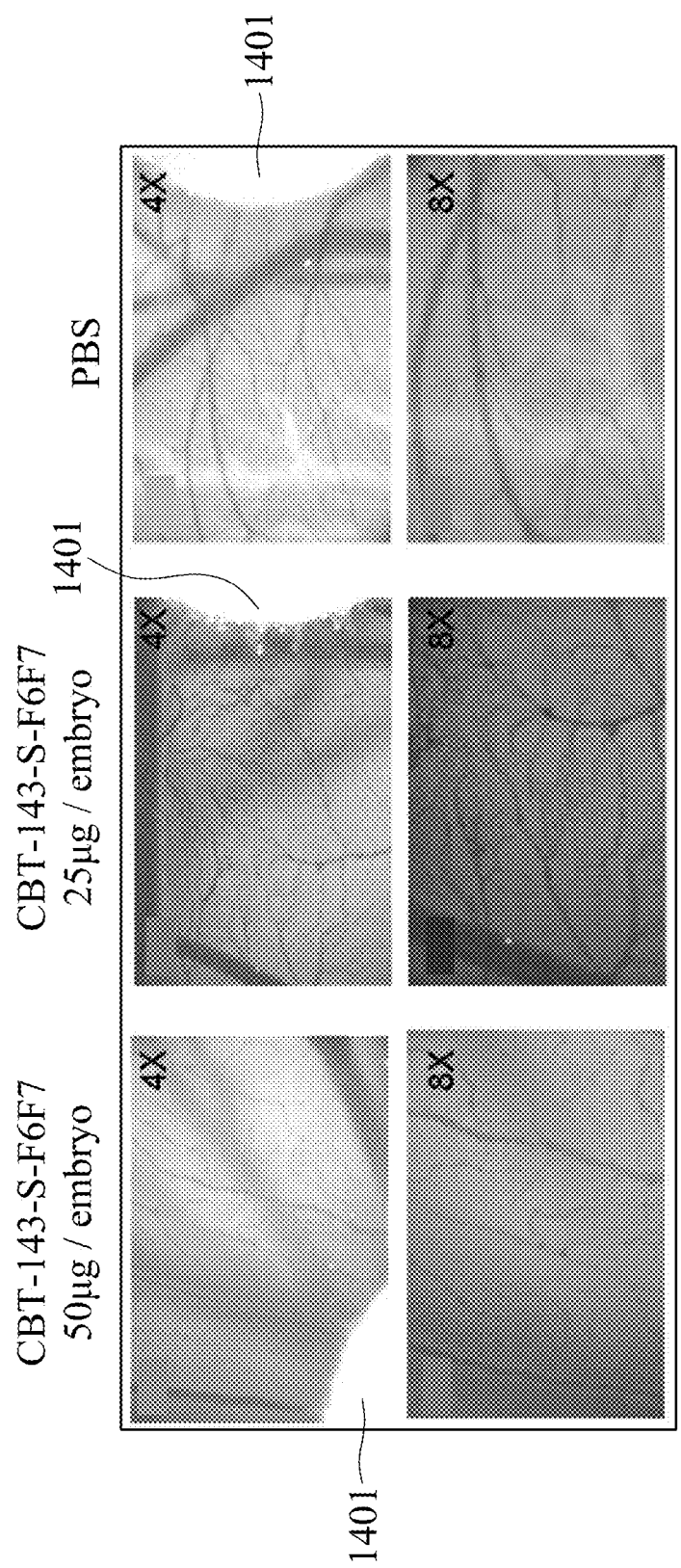
FIG. 16 shows the effect of the fractional extract, CBT-143-S-F6F7, on angiogenesis in a living body (4× and 8× magnification). Reference number 1401 in FIG. 16 refers to filter paper containing a test drug according to one embodiment of the disclosure.

The Experimental Results:

According to Table 2 and FIG. 15, the fractional extract (CBT-143-S-F6F7) (25 µg/embryo) and the crude extract (CBT-143-S) (50 µg/embryo) all resulted in a significant decrease in the angiogenesis of the chorioallantoic membrane. In FIG. 15, reference number 1301 refers to filter paper containing a test drug. Furthermore, according to FIG. 16, it was found that moderate and high dosage groups of the fractional extract (CBT-143-S-F6F7) indeed resulted in conformation change for capillary vessels. In FIG. 16, reference number 1401 refers to filter paper containing a test drug.

TABLE 2

Results of in vivo anti-angiogenesis experiment (Chorioallantoic membrane (CAM) assay)

| Test drug (in 1% DMSO) | µg/embryo | Number Death/ test embryo | N (for VDI) | VDI (in 106.8 mm) | | | p value (t-test vs PBS) |
| --- | --- | --- | --- | --- | --- | --- | --- |
| | | | | Average | Standard deviation | CV | |
| CBT-143-S-F6F7 | 50 | 4/5 | 1 | 112.3 | — | — | — |
| CBT-143-S-F6F7 | 25 | 0/6 | 6 | 119.1 | 30.1 | 0.25 | 0.023 |
| CBT-143-S-F6F7 | 10 | 0/5 | 5 | 149.3 | 40.3 | 0.27 | 0.506 |
| CBT-143-S | 50 | 1/6 | 5 | 124.5 | 20.1 | 0.16 | 0.020 |
| CBT-143-S | 25 | 1/6 | 5 | 146.5 | 22.1 | 0.15 | 0.258 |
| CBT-143-S | 10 | 1/5 | 4 | 184.6 | 9.2 | 0.05 | 0.131 |
| PBS | — | 0/6 | 5 | 163.7 | 22.7 | 0.14 | — |

7. Toxicity Tests for the Crude Extract (CBT-143-S) and the Fractional Extract (CBT-143-S-F6F7) to Normal Cells In order to investigate whether the inhibiting effects mentioned above of the crude extract (CBT-143-S) and the fractional extract (CBT-143-S-F6F7) are due to the toxicity thereof or not, cell viability assay for normal cells, PBMCs, and growth inhibition assays for HUVECs were performed to the crude extract (CBT-143-S) and the fractional extract (CBT-143-S-F6F7), and a commercial clinical drug, sorafenib, were used for comparison as a reference.

(1) Toxicity Tests for Normal Cells, PBMCs (Alamarblue Cell Viability Assay)

Alamarblue is a plant dye that is usually blue. The dye decomposes during cell proliferation and reduces from blue to pink, and a rise in O.D. at 570 nm can be determined. Conversely, the more dead cells there are, the lower the O.D. value is determined to be.

PBMC cells ($1 \times 10^5$ cells/well) were inoculated in a 96-well plate, and the crude extract (CBT-143-S) and the fractional extract (CBT-143-S-F6F7) samples, etc. with different concentrations (300, 100, 30, 10, 3 and 1 μg/mL) were added to the plate. After incubating for 72 hours, Alamarblue was added to the plate and incubated at 37° C. for 24 hours, and then the O.D. at 570 nm/600 nm thereof was determined by an ELISA reader. After that, the obtained O.D. values were substituted into the formal calculation as follows:

$$\text{Percent difference in reduction} = \frac{(\varepsilon_{OX})\lambda_2 A\lambda_1 - (\varepsilon_{OX})\lambda_1 A\lambda_2 \text{ of test agents dilution}}{(\varepsilon_{OX})\lambda_2 A^0\lambda_1 - (\varepsilon_{OX})\lambda_1 A^0\lambda_2 \text{ untreated positive growth control}} \times 100$$

$\lambda_1 = 570$
$\lambda_2 = 600$
$(\varepsilon_{OX})\lambda_2 = 117{,}216$ (OX represents oxidation)
$(\varepsilon_{OX})\lambda_1 = 80{,}586$
$A\lambda_1 = 0.65$ Observed absorbance reading for the test well
$A\lambda_2 = 0.36$ Observed absorbance reading for the test well
$A^0\lambda_2 = 0.78$ Observed absorbance reading for the positive control well
$A^0\lambda_1 = 0.19$ Observed absorbance reading for the positive control well The results showed that when the concentration of the fractional extract (CBT-143-S-F6F7) was 30 ug/ml, cell viability of PBMCs was still higher than 50%, and that showed that $IC_{50}$ of the fractional extract (CBT-143-S-F6F7) was greater than 30 ug/mL (Table 3).

Toxicity tests for the crude extract (CBT-143-S) and the fractional extract (CBT-143-S-F6F7) to normal cells, PBMCs

| | $IC_{50}$ of a test drug for PBMCs | |
|---|---|---|
| CBT-143-S (ug/mL) | CBT-143-S-F6F7 (ug/mL) | Sorafenib (uM) |
| $IC_{50}$ >30 | >30 | 10.75 ± 0.95 |

(2) Inhibition Analysis for HUVEC Growth

Figure 17:
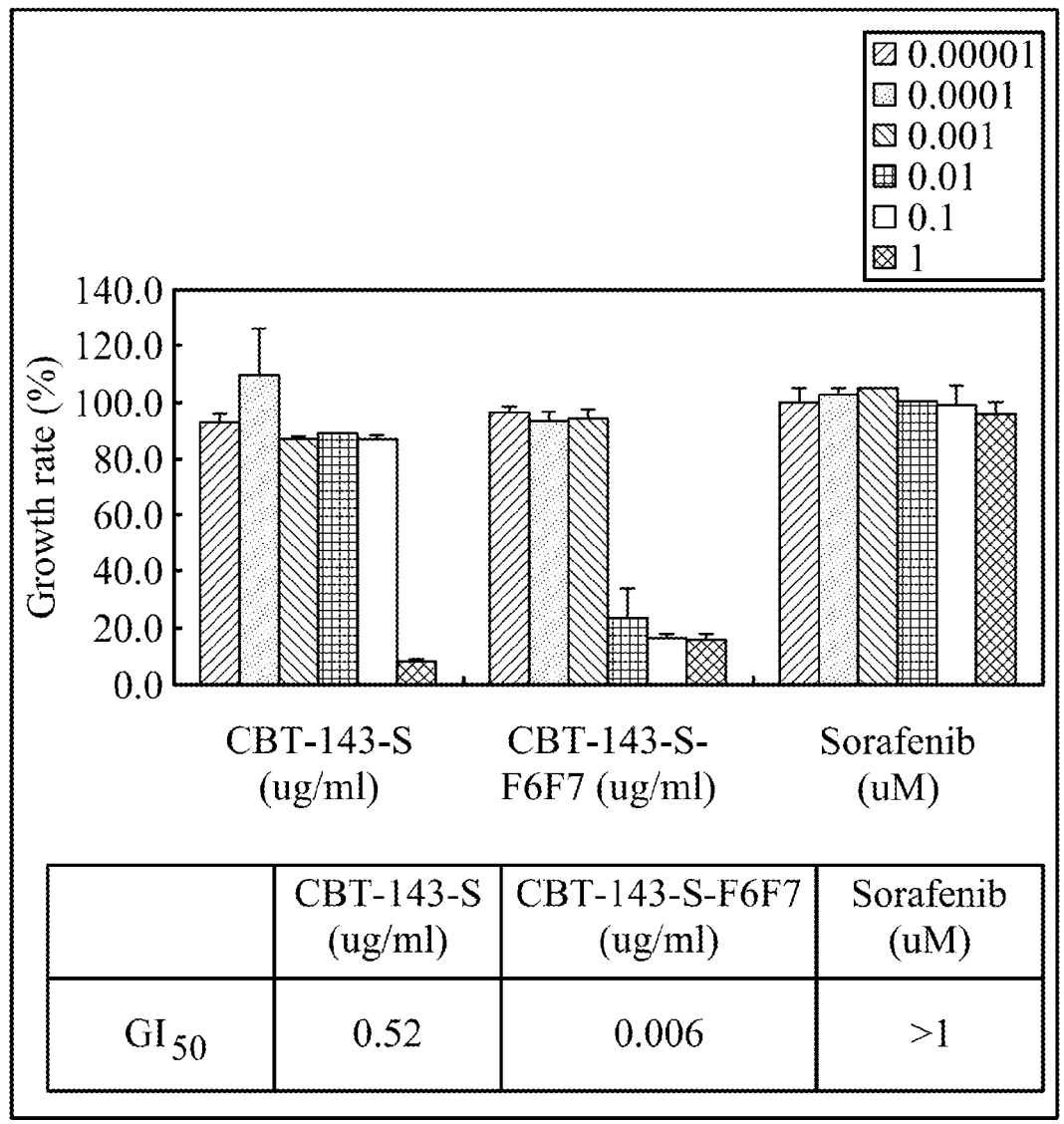
FIG. 17 shows the effects of the fractional extract, CBT-143-S-F6F7, and the crude extract, CBT-143-S, on cell proliferation of HUVEC cells according to one embodiment of the disclosure.

Similarly, an Alamarblue assay was used to evaluate cell viability. HUVEC cells ($1 \times 10^4$ cells/well) were inoculated in a 96-well plate. The crude extract (CBT-143-S) and the fractional extract (CBT-143-S-F6F7) samples, etc. with different concentrations (300, 100, 30, 10, 3 and 1 μg/mL) were added to the plate, and absorbance at 0 hours and 48 hours was record to evaluate whether cell growth was affected by the test drug or not. The results showed that 50% growth inhibition concentration ($GI_{50}$) of the crude extract (CBT-143-S) and the fractional extract (CBT-143-S-F6F7) were 0.52 ug/mL and 0.006 ug/mL (FIG. 17). According to the above-mentioned, the inhibition phenomenon of *Juniperus chinensis* L. var. *sargentii* Henry extract to the growth of HUVEC was very obvious.

8. Rat Corneal Neovascularization Assay

Pellets made of the hydron polymer (polyHEME) and a test drug or DMSO were implanted on the corneal surface of rats, and vascular formation thereof was observed.

A hydron polymer (polyHEME) was dissolved in absolute ethanol (12% w/v) in a rotator at 37° C. overnight, and then stored at room temperature before pellet making. Each pellet for the corneal pocket assay contained 60 ng of bFGF, or 1 ug JC-5 and 20 ug of sucralfate in 3 uL of casting gel, which was constituted as a 50:50 (vol/vol) mixture of hydron gel and factor-sucralfate-PBS. The casting gel was promptly pipetted onto an autoclaved, sterilized 20×20-mm piece of nylon mesh with an approximate pore size of 2×2 mm. The pellets were prepared the day before corneal surgery in a laminar flow hood under sterile conditions. Subsequently, the fibers of the mesh were pulled apart, and uniformly sized pellets of 2×2×0.4 mm$^3$ were selected for implantation. All procedures were performed in sterile conditions. Such pellets can be stored frozen at −20° C. for several days without loss of bioactivity. Each group contained six eyes. Male rats (Sprague Dawley, purchased from National Laboratory Animal Center, Taiwan.) were anesthetized with ketamine, eyes were topically anesthetized with 0.5% proparacaine. Using an operative microscope, we performed a central intrastromal linear keratotomy (~2.5 mm in length) with a surgical knife at the 12 o'clock position. A lamellar micropocket was dissected to 2 mm near the limbus. The pellet was advanced to the end of the pocket. Antibiotic ointment (erythromycin) was applied once to the surgical eye to prevent infection and to decrease irritation of the irregular ocular surface. 7 and 14 days after pellet implantation, the rats were anesthetized with ketamine. The eyes were exposed, and the maximum vessel length (VL) of the neovascularization zone, extending from the base of the limbal vascular plexus toward the pellet, was measured. Photographs were taken. The contiguous circumferential zone of neovascularization (CN) was measured in clock hours with a 360° reticule (where 30° of arc equals 1 clock hour).

Figure 18A:
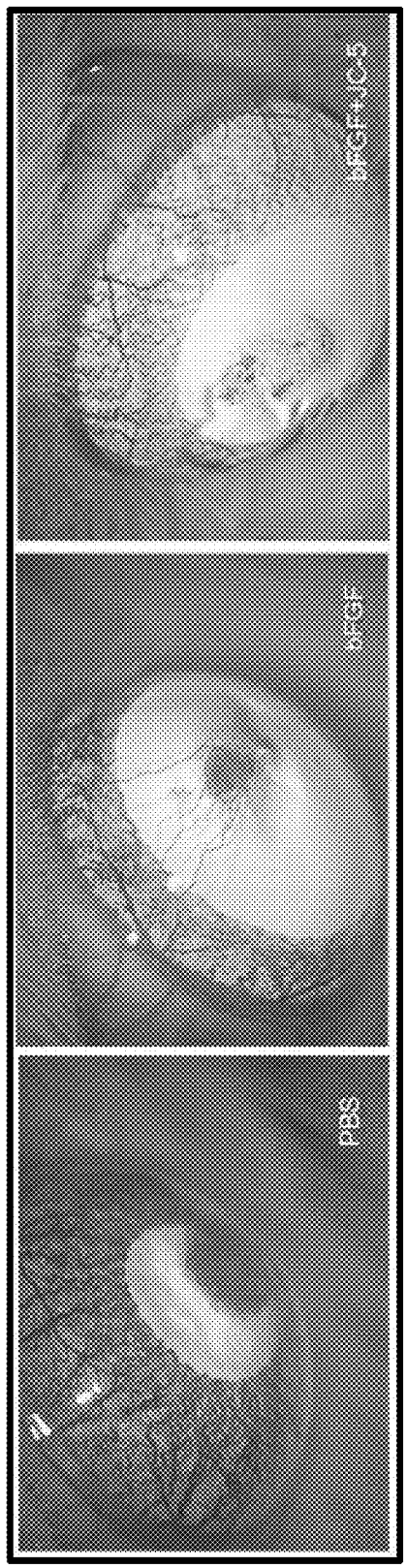
FIGS. 18A, 18B, and 18C show the effect of the compound, JC-5, on rat corneal neovascularization according to one embodiment of the disclosure.
Figure 18B:
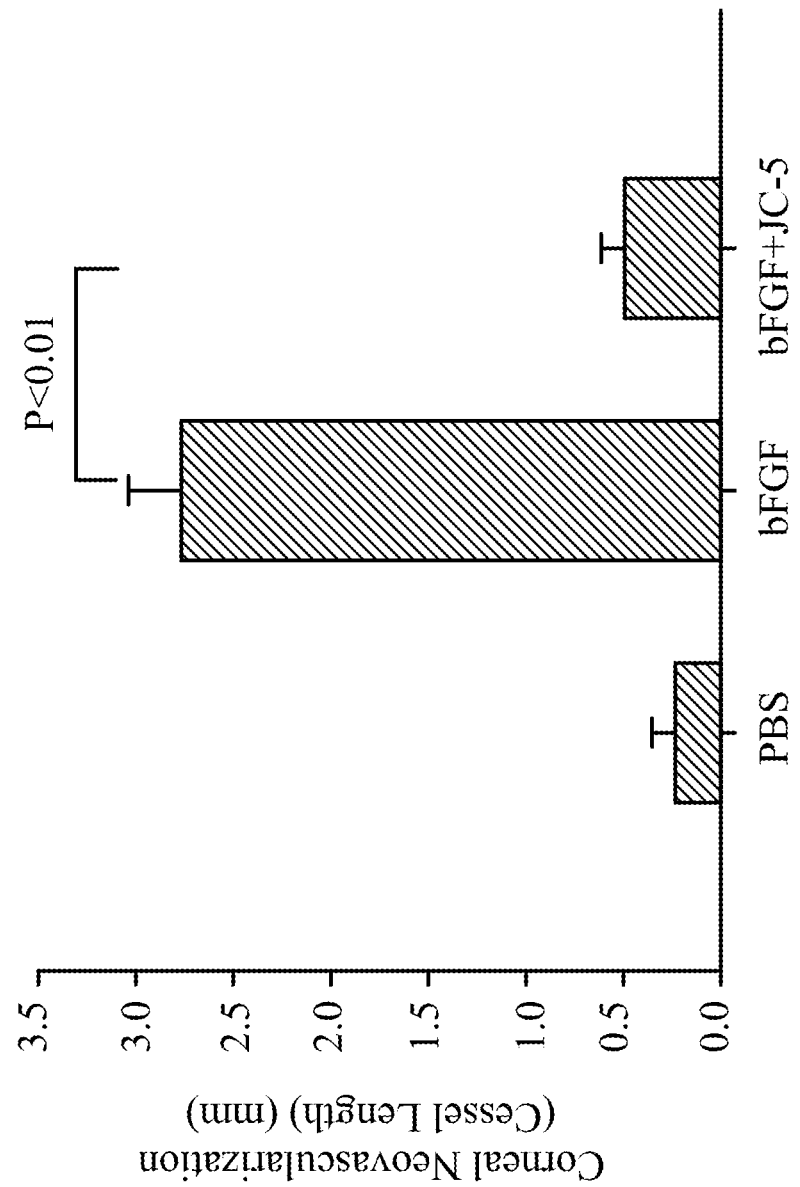
Figure 18C:
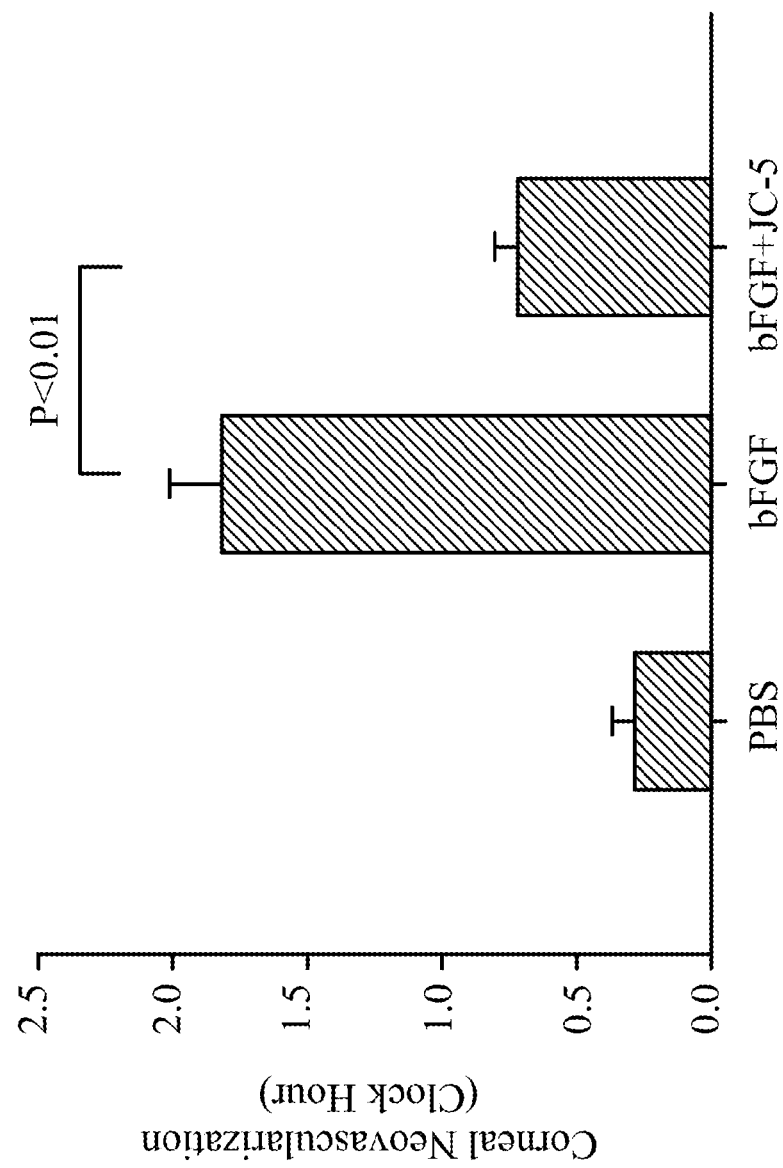

The Experimental Results:

Pellets containing the slow-release polymer hydron with PBS alone, bFGF alone, or bFGF plus JC-5 were implanted in rat corneas. Pellets containing PBS alone (N=6 eyes in all groups) did not induce neovascularization (FIGS. 18A, 18B and 18C, PBS). Pellets containing 60 ng of bFGF induced neovascularization on postoperative day 7 (FIGS. 18A, 18B and 18C, bFGF). The neovascular response was inhibited in implanted cornea with 60 ng of bFGF plus 1 ug JC-5 on day 7 (FIGS. 18A, 18B and 18C, bFGF+JC-5). These results showed JC-5 inhibited corneal neovascularization in a rat corneal pocket assay.

9. Laser-Induced Choroidal Neovascularization (CNV) Assay.

Male rats (brown Norway rats, purchased from Bio-LASCO Co., Taiwan) were used. CNV lesions were induced in rat eyes by laser photocoagulation. Briefly, after the rats were anesthetized, their pupils were dilated with 1% tropicamide. A piece of 18×24 mm$^2$ standard cover glass served as a contact lens for application of photocoagulation. Argon laser irradiation was delivered through a slit lamp. Laser parameters were set as follows: spot size of 50 μm; power of 120 mW; and exposure duration of 0.1 second. An attempt was made to break Bruch's membrane, as clinically evidenced by central bubble formation, with or without intraretinal or choroidal hemorrhage. Four to six lesions were created between the major retinal vessels in each fundus. One day prior to laser treatment, animals received bilateral intravitreal injection of 2 ul JC-5 (1 ug/eye, N=6) or 2 ul vehicle (DMSO, N=6). Fourteen days later, a self-retaining eye speculum was placed in the eye to facilitate administration. Intravitreal injections of 2 ul of JC-5 or vehicle were administered per eye using a 30-gauge needle.

Intravitreal injections were followed by topical administration of 1-2 drops of Vigamox (0.5% moxifloxacin hydrochloride) antibacterial ophthalmic solution. Characterization of laser-induced CNV on fluorescein angiograms was performed using a digital imaging system. Rats were analyzed under general anesthesia after dilation of the pupil and subsequent intraperitoneal injection of 0.5 ml of 2.5% fluorescein sodium (Alcon, CITY, Germany). Each investigation included early phase (1-3 min after injection) images. For quantitative analysis of fluorescein leakage, the area of fluorescein leakage, determined as area of hyperfluorescence in which no normal retinal blood vessels were observed, was measured for each burn using ImageJ software (NIH, USA).

Figure 19A:
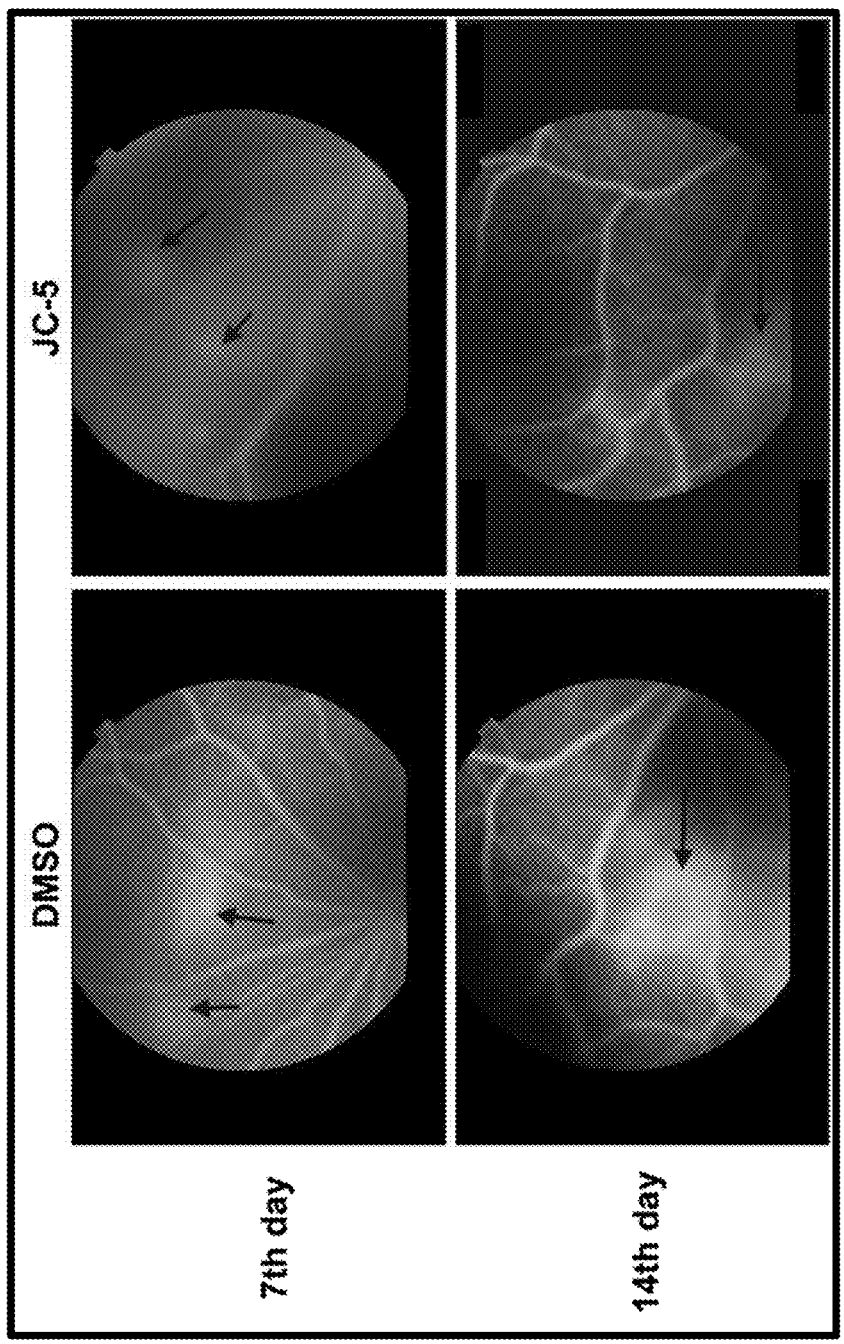
FIGS. 19A and 19B show the effect of the compound, JC-5, on laser-induced choroidal neovascularization according to one embodiment of the disclosure.
Figure 19B:
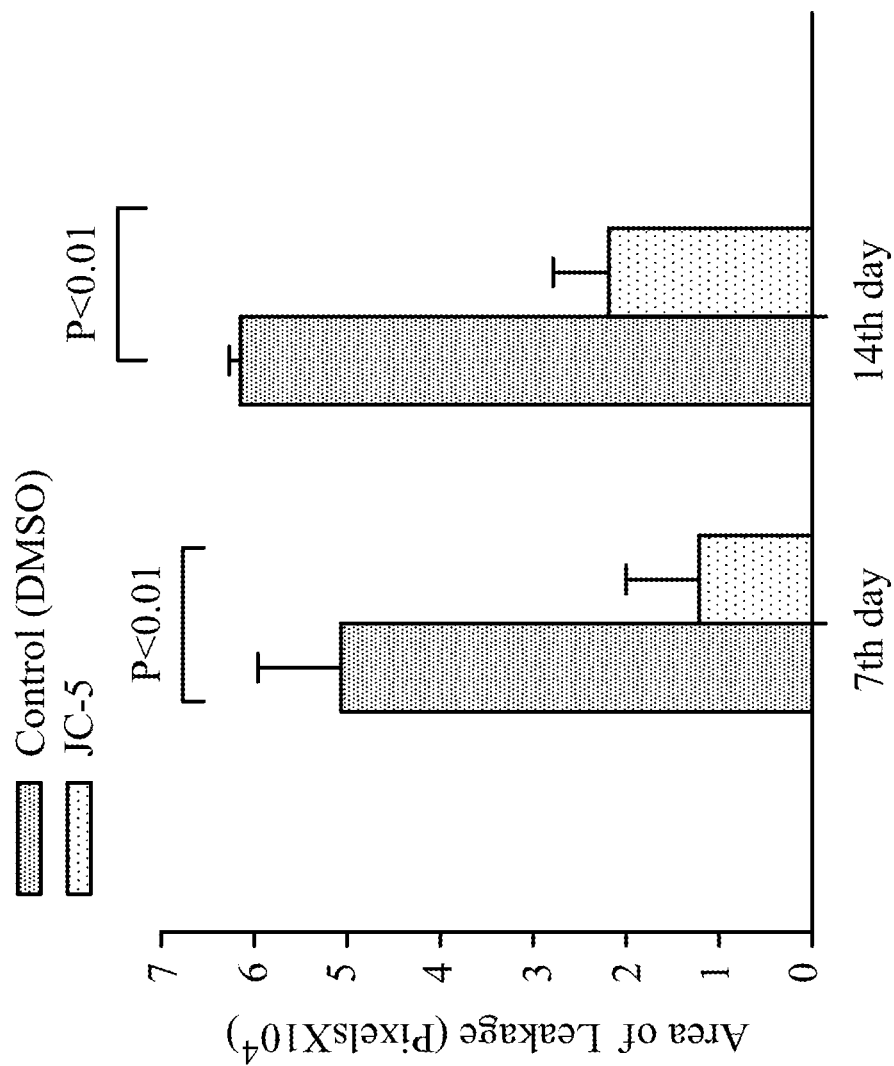

The Experimental Results:

The therapeutic efficacy of JC-5 (1 μg/2 ul in DMSO) over time was evaluated by using fluorescein angiography to analyze laser-induced CNV after JC-5 treatment. JC-5-treated eyes had less fluorescent dye uptake and extent of CNV (FIG. 19A). In addition, CNV lesions areas in JC-5-treated rats were significantly decreased on day 7 and day 14 compared to DMSO-treated vehicles (FIGS. 19A and 19B). These results indicated that topical JC-5 application attenuated the severity of experimental CNV.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for inhibiting angiogenesis in a subject in need thereof, comprising:
   administering an effective amount of a lignan to said subject, wherein the lignan has the chemical structure shown in Formula (I):

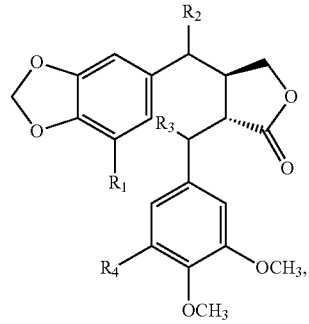

Formula (I)

wherein $R_1$ is —H or —OCH$_3$, $R_2$ is —H or —OH, $R_3$ is —H, —OH or β-O-glucoside, and $R_4$ is —H or —OCH$_3$.

2. The method for inhibiting angiogenesis as claimed in claim 1, wherein the lignan is selected from the group consisting of yatein, 5'-desmethoxyyatein (bursehernin), 7',7'-dihydroxy bursehernin, 5'-methoxyyatein, podorhizol or podorhizol 4'-o-β-D-glucopyranoside.

* * * * *